United States Patent
Ben-Haim et al.

(10) Patent No.: US 6,600,948 B2
(45) Date of Patent: Jul. 29, 2003

(54) METHOD FOR VELOCITY COMPONENT VECTOR MAPPING

(75) Inventors: Shlomo Ben-Haim, Haifa (IL); Ilan Greenberg, Haifa (IL); Boaz Bahar, Kiriat-Ono (IL)

(73) Assignee: Biosense, Inc., New Brunswick, NJ (US)

( * ) Notice: Subject to any disclaimer, the term of this patent is extended or adjusted under 35 U.S.C. 154(b) by 114 days.

(21) Appl. No.: 09/109,802

(22) Filed: Jul. 2, 1998

(65) Prior Publication Data

US 2002/0055674 A1 May 9, 2002

Related U.S. Application Data

(63) Continuation of application No. PCT/IL97/00009, filed on Aug. 1, 1997.
(60) Provisional application No. 60/009,769, filed on Jan. 11, 1996, and provisional application No. 60/011,721, filed on Feb. 15, 1996.

(30) Foreign Application Priority Data

Jan. 8, 1996 (IL) ................................................ 116699

(51) Int. Cl.$^7$ ............................................. A61B 5/0402
(52) U.S. Cl. ....................................... 600/512; 600/509
(58) Field of Search ................................ 600/509, 512, 600/515

(56) References Cited

U.S. PATENT DOCUMENTS

| 3,316,896 A | 5/1967 | Thomasset ................... 128/2.1 |
| 3,361,963 A | 1/1968 | Watson |
| 4,522,212 A | 6/1985 | Gelinas et al. ............... 128/642 |
| 4,628,937 A | 12/1986 | Hess et al. ................... 128/642 |
| 4,660,571 A | 4/1987 | Hess et al. ................... 128/784 |
| 4,682,603 A | 7/1987 | Franz .......................... 128/642 |
| 4,699,147 A | 10/1987 | Chilson et al. .............. 128/642 |
| 4,762,124 A | 8/1988 | Kerch et al. ................. 128/156 |
| 4,771,237 A | 9/1988 | Daley |
| 4,898,181 A | 2/1990 | Kessler ........................ 128/699 |
| 4,905,705 A | 3/1990 | Kizakevich et al. ......... 128/696 |

(List continued on next page.)

FOREIGN PATENT DOCUMENTS

| DE | 43 25 059 A | 1/1994 |
| WO | WO 94/00050 | 1/1994 |
| WO | WO 94/06349 | 3/1994 |
| WO | WO 95/05773 | 3/1995 |
| WO | WO 95/10226 | 4/1995 |

OTHER PUBLICATIONS

Hideo Saito et al.: "Magnetic Field Imaging Using Computer Tomography–Vector Reconstruction", Systems & Computers in Japan, US, Scripta Technica Journals, New York, vol. 21, No. 13, 1990, pp. 69–78.

(List continued on next page.)

Primary Examiner—Kennedy Schaetzle
(74) Attorney, Agent, or Firm—Louis J. Capezzuto

(57) ABSTRACT

An elongate probe apparatus (20) for insertion into the body of a subject, comprising: a structure (24) having a substantially rigid configuration; a plurality of physiological sensors (26, 28, 30), which generate signals responsive to a physiological activity, said sensors (24, 28, 30) having substantially fixed positions on said structure (24) in said configuration; and one or more devices that generate position signals indicative of the positions of the physiological sensors on said structure in said configuration.

14 Claims, 18 Drawing Sheets

U.S. PATENT DOCUMENTS

| | | |
|---|---|---|
| 4,911,174 A | 3/1990 | Pederson et al. ............ 128/695 |
| 4,922,912 A | 5/1990 | Watanabe .................... 128/642 |
| 4,940,064 A | 7/1990 | Desai ......................... 128/784 |
| 4,955,382 A | 9/1990 | Franz et al. ................ 128/642 |
| 4,962,767 A | 10/1990 | Brownlee .................... 128/786 |
| 4,979,510 A | 12/1990 | Franz et al. ................ 128/642 |
| 5,022,396 A | 6/1991 | Watanabe .................... 128/642 |
| 5,038,791 A | 8/1991 | Collins et al. .............. 128/696 |
| 5,127,403 A | 7/1992 | Brownlee ............... 128/419 P |
| 5,156,151 A | 10/1992 | Imran ......................... 128/642 |
| 5,215,103 A | 6/1993 | Desai ......................... 128/784 |
| 5,228,442 A | 7/1993 | Imran ......................... 128/642 |
| 5,231,995 A | 8/1993 | Desai ......................... 128/784 |
| 5,239,999 A | 8/1993 | Imran ......................... 128/642 |
| 5,243,981 A | 9/1993 | Hudrlik ....................... 607/11 |
| 5,255,678 A | 10/1993 | Deslauriers et al. ........ 128/642 |
| 5,255,679 A | 10/1993 | Imran ......................... 128/642 |
| 5,279,299 A | 1/1994 | Imran ......................... 128/642 |
| 5,293,869 A | 3/1994 | Edwards et al. ............ 128/642 |
| 5,297,549 A | 3/1994 | Beatty et al. ............... 128/642 |
| 5,311,866 A | 5/1994 | Kagan et al. ............... 128/642 |
| 5,313,943 A | 5/1994 | Houser et al. .............. 128/642 |
| 5,324,284 A | 6/1994 | Imran ......................... 606/15 |
| 5,341,807 A | 8/1994 | Nardella ..................... 128/642 |
| 5,345,936 A | 9/1994 | Pomeranz et al. .......... 128/642 |
| 5,383,917 A | 1/1995 | Desai et al. ................ 607/702 |
| 5,391,199 A | 2/1995 | Ben-Haim .................. 607/122 |
| 5,433,198 A | 7/1995 | Desai ......................... 128/642 |
| 5,450,846 A | 9/1995 | Goldreyer ................... 128/642 |
| 5,454,370 A | 10/1995 | Avitall ........................ 128/642 |
| 5,465,717 A | 11/1995 | Imran et al. ................ 128/642 |
| 5,471,982 A | 12/1995 | Edwards et al. ............ 128/642 |
| 5,485,849 A | 1/1996 | Panescu et al. ............. 128/699 |
| 5,487,391 A | 1/1996 | Panescu ...................... 128/699 |
| 5,497,082 A | 3/1996 | Hancock |
| 5,546,940 A * | 8/1996 | Panescu et al. ............. 600/374 |
| 5,549,109 A | 8/1996 | Samson et al. ............. 128/642 |
| 5,555,883 A | 9/1996 | Avitall ........................ 128/642 |
| 5,558,091 A | 9/1996 | Acker et al. |
| 5,595,183 A | 1/1997 | Swanson et al. ............ 128/697 |
| 5,637,090 A | 6/1997 | McGee et al. ................ 604/95 |
| 5,657,755 A | 8/1997 | Desai ......................... 128/642 |
| 5,697,377 A | 12/1997 | Wittkampf .................. 128/696 |
| 5,730,704 A | 3/1998 | Avitall ........................ 600/374 |
| 5,755,664 A | 5/1998 | Rubenstein ................. 600/377 |
| 5,842,984 A | 12/1998 | Avitall ........................ 600/374 |
| 5,889,524 A | 3/1999 | Sheehan et al. ............. 345/419 |

OTHER PUBLICATIONS

Gerstenfeld E., Sahakian A., Baerman J., Ropella K., Swiryn S. (1991) Detection of Changes in Atrial Endocardial Activation With Use of an Orthogonal Catheter. JACC. vol. 18, No. 4: 1034–1042.

Gerstenfeld E., Sahakian A., Swiryn S. (1992) Evidence for Transient Linking of Atrial Excitation During Atrial Fibrillation in Humans. Circulation. vol. 86, No. 2: 375–382.

Kadish A., Spear J., Levine J., Hanich R., Prood C., Moore E. (1986) Vector Mapping of Myocardial Activation. Circulation. vol. 74, No. 3: 603–615.

* cited by examiner

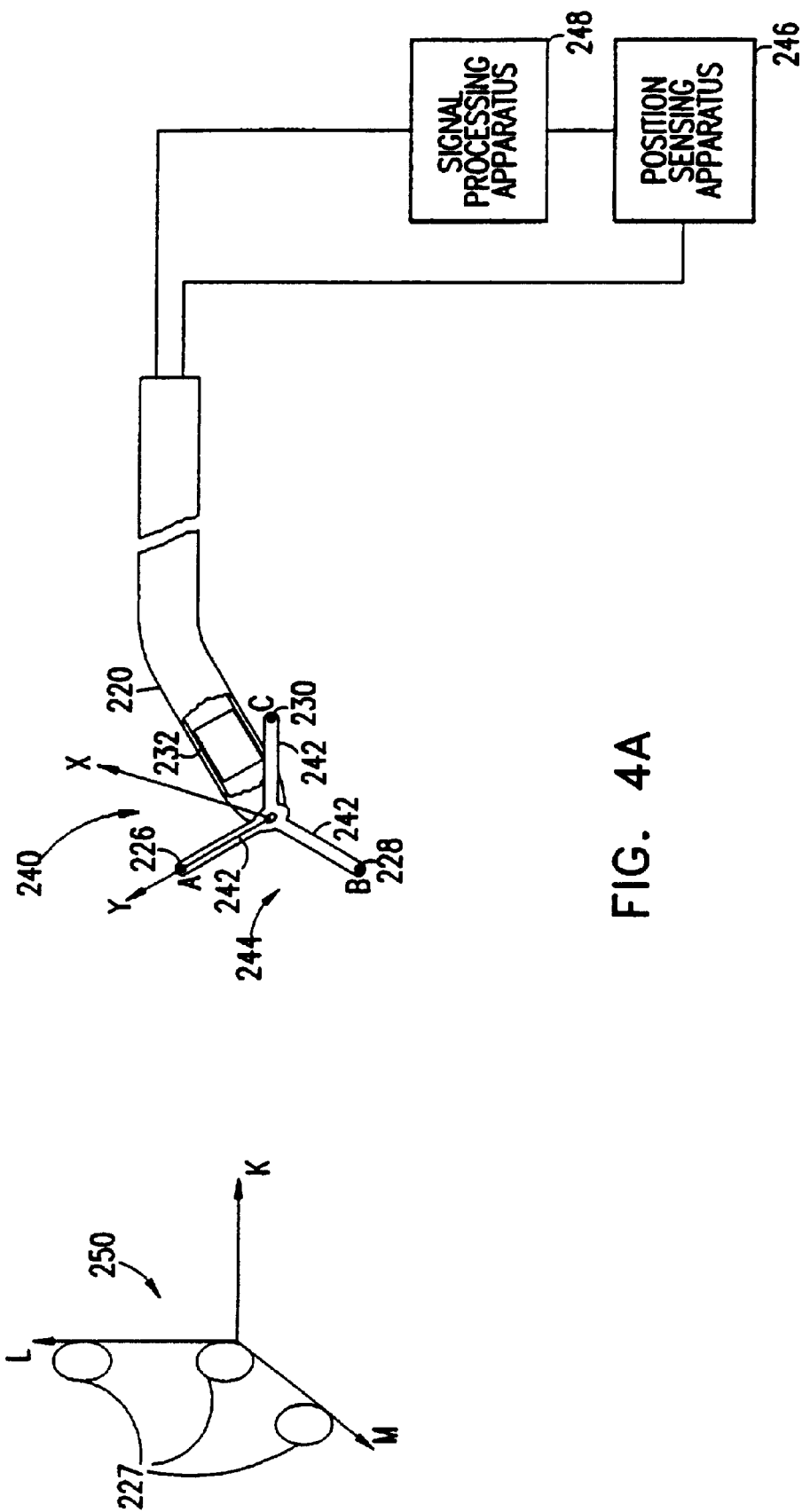

METHOD FOR VELOCITY COMPONENT VECTOR MAPPING

This application is a continuation of PCT Application No. PCT/IL97/00009 filed Aug. 1, 1997, which claims the benefit of U.S. Provisional Application Ser. Nos. 60/009,769, filed Jan. 11, 1996 and 60/011,721, filed Feb. 15, 1996; U.S. patent application Ser. No. 08/595,365, filed Feb. 1, 1996, now issued as U.S. Pat. No. 5,738,096; and Israel Patent Application No. 116699, filed Aug. 1, 1996, the entire disclosure of each is hereby incorporated by reference.

FIELD OF THE INVENTION

The present invention relates generally to medical electrophysiology systems, and specifically to invasive medical probes that may be used to map the electrical activity of the heart.

BACKGROUND OF THE INVENTION

Cardiac catheters comprising electrophysiological sensors are known for mapping the electrical activity of the heart. Typically the time-varying electrical potentials in the endocardium are sensed and recorded as a function of position inside the heart, and then used to map the local electrogram or local activation time. Activation time differs from point to point in the endocardium due to the time required for conduction of electrical impulses through the heart muscle. The direction of this electrical conduction at any point in the heart is conventionally represented by an activation vector, which is normal to an isoelectric activation front, both of which may be derived from a map of activation time. The rate of propagation of the activation front through any point in the endocardium may be represented as a velocity vector.

Mapping the activation front and conduction fields aids the physician in identifying and diagnosing abnormalities, such as ventricular and atrial tachycardia and ventricular and atrial fibrillation, that result from areas of impaired electrical propagation in the heart tissue. Localized defects in the heart's conduction of activation signals may be identified by observing phenomena such as multiple activation fronts, abnormal concentrations of activation vectors, or changes in the velocity vector or deviation of the vector from normal values. Furthermore, there may be no electrical propagation at all within defective portions of the heart muscle that have ceased to function, due to local infarction, for example. Once a defect is located by such mapping, it may be ablated (if it is functioning abnormally) or otherwise treated so as to restore the normal function of the heart insofar as is possible.

Mapping of the electrical activation time in the heart muscle requires that the location of the sensor within the heart be known at the time of each measurement. Such mapping may be performed using a single movable electrode sensor inside the heart, which sensor measures activation time relative to a fixed external reference electrode. This technique, however, gives maps of low resolution and relatively poor accuracy, limited by the accuracy of determination of the position of the electrode at the time of each measurement. The natural movement of the heart makes it very difficult to maintain an accurate reading of the position of the moving electrode from beat to beat. Mapping of electrical activation time using a single electrode is, furthermore, a lengthy procedure, which must generally be performed under fluoroscopic imaging, thereby exposing the patient to undesirable ionizing radiation. Further, in an arrhythmic heart, activation times at a single location may change between consecutive beats.

Because of these drawbacks of single-electrode mapping, a number of inventors have taught the use of multiple electrodes to measure electrical potentials simultaneously at different locations in the endocardium, thereby allowing activation time to be mapped more rapidly and conveniently, as described, for example, in PCT patent publication WO 95/05773, whose disclosure is incorporated herein by reference. In this case, the positions of all the electrode sensors must be determined at the time of measurement, typically by means of fluoroscopic or ultrasonic imaging. These methods of position determination, however, are complicated, inconvenient and relatively inaccurate, therefore limiting the accuracy of mapping.

Alternatively, U.S. Pat. Nos. 5,471,982 and 5,465,717, whose disclosures are incorporated herein by reference, teach the use of an electrode basket, which is inserted into a chamber of the heart and then expanded so that a plurality of electrodes are simultaneously brought into contact with multiple points on the endocardium. The relative electrical activation times at all the electrodes may then be measured simultaneously and used to detect and localize abnormalities. The basket is of limited usefulness in creating high-resolution maps of the electrical activation vector, however, because it cannot easily be repositioned once it is expanded inside the heart, and furthermore, determining the absolute positions of the electrodes requires the use of fluoroscopy or other painstaking and undesirable imaging methods. Further, the basket catheter does not contract with the heart, so the electrodes in the basket catheter cannot maintain contact with the same portion of the myocardium for the entire cycle, and the electrodes may not return to the same position relative to the myocardium for each cycle.

U.S. Pat. No. 5,487,391, to Panescu, for example, describes a multiple electrode probe for deployment inside the heart. Signals received from the multiple electrodes are used for deriving the propagation velocity of depolarization events. This patent makes no provision, however, for independently determining the positions of the electrodes relative to an external or heart-fixed frame of reference, and the velocity is derived relative to the probe, rather than to the heart itself.

Detecting the position in space of a single electrophysiology mapping electrode is described, inter alia, in PCT patent application number PCT/US95/01103, filed Jan. 24, 1995, U.S. provisional application 60/009,769, filed Jan. 11, 1996, U.S. patent application Ser. No. 08/595,365, filed Feb. 1, 1996, both titled "Cardiac Electromechanics", and U.S. Pat. No. 5,391,199, issued Feb. 21, 1995, the disclosures of all of which are incorporated herein by reference.

U.S. Pat. No. 5,450,846, whose disclosure is incorporated herein by reference, describes a catheter, which may be easily repositioned inside the heart, comprising an ablator at its distal tip and pairs of non-contacting sensing electrodes arrayed around the outside of the catheter near the distal end. Each electrode senses local electrogram signals generated in the endocardium in a small area near the side of the catheter that it faces. Differences in the activation times in the signals sensed by the pairs of electrodes are used to estimate the direction of the activation vector in the vicinity of the catheter, so as to guide the operator in positioning the ablator. However, use of this device in high-resolution mapping of activation vectors is not practical either, because of the difficulty of determining the absolute position of the catheter tip, which must be performed by imaging methods, and because of the inferior accuracy of the non-contact electrogram measurement.

PCT publication WO/95/10226 describes a catheter that includes a ring at its distal end, designed to bear against the circumference of a valve of the heart. The ring comprises electrodes, which measure electrical activity in the valve tissue. When abnormal electrical activity is detected in the valve tissue adjacent to one of the electrodes, an electrical current is applied through the electrode so as to ablate the tissue at the site of the abnormal activity. The invention provides no means for determination of the position of the ring and electrodes, however, other than methods of imaging known in the art, and is therefore not useful for mapping electrical activity, nor is it useful in areas of the heart other than the valves.

U.S. Pat. No. 5,555,883, to Avitall, the disclosure of which is incorporated herein by reference, describes a catheter with a loop shaped mapping and ablation system. There is no provision, in this patent, for determining the position of individual electrodes relative to the heart surface being mapped/ablated.

SUMMARY OF THE INVENTION

It is an object of the present invention to allow simultaneous measurement of physiological signals by multiple sensors inside a human body, while simultaneously providing accurate measurement of at least the relative locations of all the sensors.

In one aspect of the invention, the sensors are fixed to a catheter, and the locations of the sensors are measured by determining the position of a device in the catheter that generates position and orientation information.

A further object of the present invention is to provide a method and a device for rapidly and accurately measuring local electrical propagation vectors in the heart muscle, in order to locate sites of abnormal electrical propagation, for purposes of subsequent diagnosis and therapy.

In a preferred embodiment of the present invention, a plurality of electrodes are attached to a structure at the distal end of a catheter. One or more devices for generating position information are placed in proximity to the electrodes, so that the positions of all the electrodes can be determined in relation to an external frame of reference or relative to the heart. The position information and signals measured by the electrodes are used to determine the direction and magnitude of the electrical activation vector at the location of the structure at the distal end of the catheter.

In preferred embodiments of the present invention, the structure at the distal end of the catheter comprises at least three non-collinear electrodes, so that the direction of the electrical activation vector in the plane defined by the electrodes may be fully determined.

In some preferred embodiments of the present invention, the electrodes are attached to a substantially rigid ring at the distal end of a catheter. A device that generates position information is coupled to the ring, so that the position and rotational orientation of the ring may be determined, thus determining the locations of all the electrodes. Alternatively or additionally, the geometrical shape and angular orientation of the ring are known relative to the catheter. If the locations of the electrodes relative to the catheter are substantially predetermined, the positions of all the electrodes may be determined from a determined position and orientation of the catheter tip. Further, in this case, it is sufficient to determine the location of the tip and only the rotational coordinate of the catheter tip around its axis.

A catheter of the present invention is preferably inserted into a chamber of the heart. The ring at the distal end of the catheter is placed in contact with the endocardium, and the electrical propagation vector is measured at the location of the ring. The distal end of the catheter may then be repeatedly repositioned to other locations on the endocardium, so as to generate a map of the propagation vector field or to locate an area of abnormality.

In the context of this invention, the term substantially rigid, as applied to the ring at the distal end of the catheter, is taken to mean that during successive measurements of electrophysiological signals by the electrodes, the shape of the ring and its angular orientation relative to the long axis of the catheter remain fixed in a known, predetermined relation. Consequently, the location of each of the electrodes on the ring relative to a coordinate information device is fixed and known, and thus the locations of all the electrodes relative to an external reference frame may be determined using the location and orientation information provided by the coordinate information device. However, in some embodiments of the invention, where individual electrodes are fixed to the myocardium, such as when using extendible barbs to hold the electrodes in place, the electrodes are allowed to move relative to each other, as a result of myocardial contraction.

Although the substantially rigid ring maintains its shape during measurements, for purposes of insertion and removal of the catheter the ring may be straightened or flattened, so as to pass easily through narrow channels, such as blood vessels, or through a lumen of the catheter.

In a preferred embodiment of the present invention, the substantially rigid ring is formed of a resilient, super-elastic material, such as NiTi. For insertion or removal of the catheter from the body, the ring is compressed inside a narrow sleeve adjacent to the distal end of the catheter. After insertion of the catheter, the ring is ejected from the sleeve and assumes its predetermined shape and position.

In one preferred embodiment of the invention, the substantially rigid ring is made from a flat, ribbon-like section of resilient material. The distal end of the catheter, with which the ring is in contact after it has been ejected from the sleeve, is likewise flat and includes a slot necessary for ejection of the ring. Thus once the ring is ejected, it is substantially prevented from rotating or tilting relative to the axis of the catheter and does not substantially bend or deform under the forces exerted on it during successive measurements inside the heart. In this manner the positions of the electrodes on the ring are maintained in predetermined relations to the distal end of the catheter.

In another preferred embodiment of the present invention, the ring is formed of a hollow section of resilient, super-elastic material, which is rigidly coupled to the distal end of the catheter at a known angular orientation. For insertion or removal of the catheter from the body, the ring is straightened by insertion of a stylette into the lumen of the hollow section. After insertion of the catheter into the heart, the stylette is withdrawn, and the ring reassumes its predetermined shape and orientation.

In an alternative preferred embodiment of the present invention, the ring at the distal end of the catheter is formed of a hollow section of flexible material, which is straightened for insertion or removal of the catheter from the body by insertion of a straight stylette into the lumen of the hollow section. After the straight stylette is withdrawn, a second stylette, formed of substantially rigid, resilient material and including a curved portion at its distal end, is inserted. For insertion of this second stylette through a lumen of the catheter, the curved distal portion of the stylette is straightened, and the relative stiffness of the catheter causes the stylette to remain straight. When this stylette reaches the hollow, flexible section at the distal end of the catheter, however, the resilience of the stylette causes its distal portion to resume its curved shape, and thus causes the hollow, flexible section of the catheter to curve, as well, into the desired ring shape.

In some preferred embodiments of the present invention in which the distal end of the catheter is straightened during insertion into the heart, when the section at the distal end of the catheter is caused to curve into a ring shape after insertion, the distal tip of this section engages a socket in the side of the catheter. Fluoroscopy or other methods of imaging known in the art may be used to observe the ring at the distal end of the catheter and verify that the distal tip of the distal section has engaged the socket, so as to ensure that the ring has assumed its desired shape and orientation prior to beginning electrophysiological measurements.

Alternatively, in some preferred embodiments of this type, the distal tip of the distal end section of the catheter comprises a first electrical contact, and the socket in the side of the catheter comprises a second electrical contact. When the distal tip engages the socket, the first electrical contact is brought into proximity with the second electrical contact. The mutual proximity of the contacts is measured electrically using methods known in the art, so as to verify that the distal tip has engaged the socket.

In other preferred embodiments of the present invention, the structure to which the electrodes are attached at the distal end of the catheter may comprise a ring of any desired cross-sectional profile, or the structure may be formed in a shape of non-uniform profile. In one such preferred embodiment, the structure comprises rigid sections, to which the electrodes are attached, and flexible, resilient sections between the rigid sections. The flexible, resilient sections allow the structure to be easily collapsed for passage through the blood vessels, and then cause the structure to resume its desired shape for making measurements when released inside a chamber of the heart.

In still other preferred embodiments of the present invention, the structure to which the electrodes are attached at the distal end of the catheter is polygonal, most preferably triangular with sharp vertices. When the sharp vertices of the polygonal structure are brought into contact with the endocardium, they will typically lodge in small crevices in the heart tissue, thus preventing the structure from moving during measurement, despite the natural motion of the heart. The electrodes are preferably at the vertices.

In other preferred embodiments of the present invention, the structure in which the electrodes are placed at the distal end of the catheter comprises multiple arms, wherein electrodes are fixed to the arms. During insertion of the catheter into the heart, the arms are held parallel and adjacent to the long central axis of the catheter. Once inside the heart, the arms spread apart, away from the long axis of the catheter at predetermined, known angles.

In one such embodiment of the present invention, each arm is formed of at least two sections of substantially rigid material, connected together by a resilient joint. The arms are joined at their proximal ends to the distal end of the catheter. A draw-wire passes through a lumen in the catheter and is attached at its distal end to the distal ends of the arms, which are joined together. During insertion of the catheter into the heart, the resilient joints tend to hold the arms straight and parallel to the long central axis of the catheter. Once the arms are wholly inside the heart, the draw-wire is pulled back toward the proximal end of the catheter, thereby drawing in the distal ends of the arms and causing the arms to flex at their resilient joints. The draw-wire is pulled back until the joints are completely flexed, and the distal ends of the arms are brought into close proximity with the proximal ends thereof, so that the arms protrude laterally out from the long central axis of the catheter. For removal of the catheter from the heart, the draw-wire is released, and the resilient joints straighten to their original shapes.

In another such embodiment of the present invention, substantially rigid arms, having electrodes adjacent to their distal ends, are contained inside a lumen of the catheter during insertion of the catheter into the heart. Once the distal end of the catheter has been inserted into the heart, the distal ends of the arms are ejected through small radial openings, spaced around the axis of the catheter. The resilience of the arms causes them to spread apart radially away from the long central axis of the catheter and axially, distal to the distal end of the catheter.

In yet other preferred embodiments of the invention, the structure at the distal end of the catheter is a balloon or another inflatable structure, to which electrodes are fixed. After the catheter has been inserted into the heart, the structure is inflated and assumes a predetermined, known shape and orientation relative to the distal end of the catheter.

In some preferred embodiments in accordance with the present invention, the device that generates position information comprises a plurality of coils, as disclosed in PCT patent application number PCT/US95/01103, filed Jan. 24, 1995, which is assigned to the assignee of the present application and whose disclosure is incorporated herein by reference. This device continuously generates six-dimensional position and orientation information regarding the catheter tip. This system uses a plurality of non-concentric coils adjacent to a locatable site in the catheter, for example near its distal end. These coils generate signals in response to externally applied magnetic fields, which allow for the computation of six location and orientation coordinates, so that the location and orientation of the catheter in the heart are known without the need for simultaneous imaging, by fluoroscopy or ultrasound, for example. This device generates position information relative to a reference frame defined by field generator coils. In a preferred embodiment of the invention, a Carto system, available from Biosense LTD., Tirat Hacarmel, Israel, is used for determining the position of a catheter.

Other preferred embodiments of the present invention comprise one or more devices for generating three-dimensional location information, as described, for example, in U.S. Pat. No. 5,391,199, to Ben-Haim, and PCT patent application PCT/US94/08352, which are assigned to the assignee of the present application and whose disclosures are incorporated herein by reference. One or more devices for generating location information are placed in the catheter or in the structure containing the electrodes, in proximity to the electrodes. Location information generated by these devices is used to determine the positions of the electrodes.

In one such preferred embodiment of the present invention, two or more devices for generating three-dimensional location information are placed in known, mutually-spaced locations in the catheter or in the structure containing the electrodes, thereby allowing the positions of the electrodes in the structure to be determined.

The device disclosed in the aforementioned '539 patent application for generating three-dimensional location information preferably comprises a single coil. In preferred embodiments of the present invention that include a device of this type, the coil is toroidal in shape and coaxial with the long, central axis of the catheter. These embodiments thus have the advantage that the catheter may have one or more lumens, which pass through the opening at the center of the toroidal coil, while maintaining a relatively small external catheter diameter.

In some preferred embodiments of the present invention, a device, such as described above, for generating three-dimensional location information is placed in the catheter adjacent to the electrodes and is used to determine the location of the catheter inside the heart. One or more rotation measuring devices measure the angular orientation of the distal end of the catheter. Since the structure in which the electrodes are placed allows the positions and orientations of the electrodes to be known relative to the distal end of the catheter, the location information generated by the location generating device in the catheter, taken together with the measured angular orientation of the catheter, is sufficient to fully determine the locations of the electrodes in the heart.

The rotation measuring device of this embodiment may be of any suitable type known in the art. For example, shaft encoder devices adjacent to the proximal end of the catheter may be used to measure the angle of rotation of the catheter about its long central axis and/or the angle of deflection of the catheter's distal tip. This embodiment of the invention is especially useful when the path of the catheter is relatively straight.

In some preferred embodiments of the present invention, used for mapping the electrical activity of the heart, two catheters are inserted into the heart. A first catheter comprises a ring with electrodes and a device that generates position information, as described above. A second catheter comprises a device that generates position information, and is positioned in a predetermined location in a chamber of the heart, preferably at the apex of the heart. This second catheter thus allows a reference frame to be defined that is substantially fixed with respect to the heart, relative to which the position of the first catheter is determined, so that errors in position determination due to motion of the heart and the chest, due to breathing, for example, may be canceled.

In a preferred embodiment of the present invention, for use in diagnosing and treating defects in the heart's electrical conduction, the distal end of the catheter is placed in proximity to the suspected site of a defect. On the basis of the vector direction and magnitude of the electrical impulse flow vector measured at this initial site, the catheter is then moved toward the suspected defect. This procedure is repeated until the catheter reaches the site of the defect. Preferably once the defect is located by the above procedure, it is ablated or otherwise treated by methods known in the art.

While the above preferred embodiments have been described with reference to measurement of electrophysiological signals in the heart, other preferred embodiments of the present invention may be used to measure and map electrical signals in the brain or in other physiological structures.

Furthermore, in other preferred embodiments of the present invention, other sensors, such as ionic sensors, may be used instead of the electrodes to perform localized measurements and map other aspects of physiological activity.

It is another object of some embodiments of the present invention to provide a method for accurately and rapidly determining the magnitude and direction of a vector corresponding to the propagation of activity in physiological tissue.

In one aspect of the present invention, the activity is electrical activity in the heart of a subject, and the vector corresponds to the local velocity of an electrical activation signal. In other aspects of the present invention, the vector corresponds to an ionic current caused by repolarization of the heart tissue, or to currents associated with other elements of the cardiac cycle.

In other aspects of the present invention, the activity is ionic activity or mechanical activity, such as contraction of muscle tissue, and the vector corresponds to the local ionic or isotonic current, respectively.

In a further aspect of the present invention, the magnitude and direction of the vector are determined at a plurality of known locations, and are used to generate a map of the vector as a function of location and/or as a function of time.

In preferred embodiments of the present invention, a plurality of electrodes are placed in known positions adjacent to a location in the endocardium. Electrical signals received from the plurality of electrodes are used to determine local activation times at the respective positions thereof. A local velocity vector is then calculated by comparison of the relative values of the local activation time at the positions of the electrodes.

In preferred embodiments of the present invention, the plurality of electrodes comprises at least three electrodes. The local velocity vector is determined by finding velocity vector components along two non-parallel axes, wherein each of the axes is defined by a pair of the electrodes. Vector arithmetic operations are applied to the velocity vector components to find the direction and magnitude of the local velocity vector.

In preferred embodiments of the present invention, the velocity vector component along each of the axes defined by a pair of electrodes is found by dividing the distance between the electrodes by the difference in their activation times. However, if the difference in activation times between a first pair of electrodes is substantially zero, while the difference in activation times between a second pair of electrodes is not zero, then the local velocity vector is found to be perpendicular to the axis defined by the first pair of electrodes. If all the electrodes have substantially the same activation time, then the local velocity vector is found to be zero, and the location in the endocardium to which the electrodes are adjacent is determined to contain a suspected site of pathology, for example, a sink or source of local electrical activation.

In preferred embodiments of the present invention, the local velocity vector is mapped at a plurality of locations in the heart by placing the electrodes at the plurality of locations in succession, and determining the local velocity vector at each location. Preferably the mapping of the local velocity vector is used to determine locations of defects in the propagation of electrical activation in the endocardium, and particularly to find sources and sinks of the activation.

Although preferred embodiments of the present invention are described with reference to certain types of catheter and position-sensing apparatus, it will be understood that the inventive principles of the present invention will be equally applicable to other types of probes and to other apparatus and methods, such as ultrasound or fluoroscopic imaging, for determining the positions of sensors attached to the probes.

Alternatively, the inventive principles of the present invention may be applied to measure a local velocity vector without determining the positions or orientations of sensors used in the measurement relative to an external frame of reference. This measurement is useful, for example, in identifying local conduction defects. On the basis of the vector direction of the electrical impulse flow vector measured at an initial site, the catheter is then moved toward the suspected defect. This procedure is repeated until the catheter reaches the site of the defect. Preferably once the defect is located by the above procedure, it is ablated or otherwise treated by methods known in the art.

It will further be understood that although preferred embodiments of the present invention are described with reference to measurement and mapping of electrical activation in the endocardium, the inventive principles of the present invention will be equally applicable to measurement and mapping of the propagation of other signals in the heart, such as isotonic currents and injury currents, as are known in the art. Similarly, these inventive principles may be applied to measurement and mapping of other physiological signals, such as those arising from electrical activity in the brain, or signals received from ionic sensors.

Another aspect of the present invention relates to a soft tip catheter, which may be safely and easily inserted into a body vessel. This catheter of the present invention preferably includes a resilient cap member extending distally from a distal end of the catheter. The resilient cap member preferably includes a tuft of at least one distally extending, resilient lobe with a soft, smooth outer surface or surfaces, preferably constructed of an elastomeric material, such as rubber, latex or silicon-rubber. The cap may be an attachment to the catheter or may be formed as an extension of the catheter material.

Preferably at least one sensor is fixed to the resilient cap member, preferably at the at least one lobe. The sensors may be any type of sensor useful in sensing a physiological activity, for example, determining location and orientation of a tumor, or determining proper functioning of a heart, such as contraction time of a heart muscle, or sensing an activation signal of a heart muscle. Preferably, each lobe also includes apparatus for fixing the lobe to the myocardium, for example, an extendible barb, a lumen attached to an external vacuum pump, or a bump in the external surface of the lobe and which engages local irregularities in the heart muscle.

As the catheter is inserted into a body vessel in a distal direction, the resilient cap member and its lobes may be resiliently inverted over the distal end of the catheter. The resilient inversion of resilient cap member greatly facilitates insertion of the catheter into the vessel, and provides a high degree of insertion safety, thereby substantially eliminating the possibility of the catheter scraping an inner surface of the vessel. The cap and lobes may also be inverted by if they collide with an obstruction as a result of the distal movement of the catheter. The resilient cap member also substantially prevents accidentally puncturing, scraping or otherwise damaging the interior surfaces of a body organ.

In a preferred embodiment of the invention, the catheter includes a position sensor at the base of the tuft, for determining the position of the catheter tip. Preferably, each of the sensors on the tufts has a known position relative to the position sensor. Thus, if the position sensor provides both position and orientation information, the relative positions of all the sensors can be determined. In a preferred embodiment of the invention, the tufts are arranged so that small changes in the positions of the tuft relative to the base (for example, as a result of forward pressure) do not substantially change the relative positions of the tufts.

In a preferred embodiment of the invention, there are no sharp corners or crevasses between the tufts, so that no blood can collect and clot there.

There is therefore provided, in accordance with a preferred embodiment of the present invention, elongate probe apparatus for insertion into the body of a subject, including a structure having a substantially rigid configuration; a plurality of physiological sensors, which generate signals responsive to a physiological activity, the sensors having substantially fixed positions on the structure in the substantially rigid configuration; and one or more devices that generate position signals indicative of the positions of the physiological sensors on the structure in the substantially rigid configuration.

Preferably, the elongate probe comprises a distal end, which is inserted into the body of the subject, wherein the structure, which preferably is made of resilient material, or more preferably superelastic material, has a known shape and orientation in its substantially rigid configuration relative to the distal end of the probe.

Preferably the structure has the shape of a ring in its substantially rigid configuration, and the sensors are mutually spaced around the circumference of the ring. The structure may be made of a flat strip, formed into a ring.

Alternatively, the structure may include a hollow tube. Preferably the tube is formed of flexible material, and the structure further includes a curved stylette, insertable into the center of the hollow tube so as to cause the hollow tube to assume a curved shape.

Alternatively, the structure may have a polygonal shape, preferably triangular, in its substantially rigid configuration. Preferably the sensors are adjacent to the vertices of the structure in its substantially rigid configuration.

In other preferred embodiments of the present invention, the structure includes a multiplicity of arms, such that when the structure is in its substantially rigid configuration, the arms spread radially outward relative to an axis parallel to the long dimension of the elongate probe.

Preferably the arms include substantially rigid segments, which are coupled by resilient joints. Flexure of the joints causes the arms to spread radially outward in the substantially rigid configuration of the structure.

Alternatively, the elongate probe includes mutually spaced radial openings in its outer surface, and the arms protrude from the probe through the openings.

In other preferred embodiments of the present invention, the structure further includes an inflatable element, preferably a balloon. Inflation of the inflatable element causes the structure to assume a substantially rigid configuration. Preferably the structure further includes flexible, non-extensible wires.

Preferred embodiments of the present invention further provide that when the structure is in its substantially rigid configuration, the positions of the sensors on the structure define a plane, with a first axis perpendicular to this plane; and the elongate probe defines a second axis parallel to its long dimension. The first axis may preferably be substantially parallel to the second axis, or substantially perpendicular to it.

In some preferred embodiments of the present invention, the structure has a second configuration, in which the structure is relatively narrow and elongated. Preferably, the structure in its narrow, elongated configuration has a long axis that is substantially parallel to an axis defined by the long dimension of the elongate probe.

In preferred embodiments of the present invention in which the structure, in its substantially rigid configuration, has the shape of a ring, the elongate probe may preferably include an external sheath, defining a central cavity, and the ring is preferably constructed so as to be withdrawn into the central cavity and thus compressed into a narrow, elongated configuration.

In preferred embodiments of the present invention in which the structure includes a hollow tube, a straight stylette is preferably provided for insertion into the center of the hollow tube, so as to cause the hollow tube to assume a straight shape. Preferably the structure includes a distal tip, and the elongate probe includes a socket in its side, so that the distal tip of the structure engages the socket when the structure assumes its substantially rigid, ring-shaped configuration. More preferably, the distal tip of the structure includes a first electrical contact, and the socket in the side of the catheter includes a second electrical contact; and contact between the first and second electrical contacts is measured so as to verify that the distal tip has engaged the socket.

In preferred embodiments of the present invention that include arms made up of substantially rigid segments and flexible joints, straightening the joints preferably causes the segments to maintain a substantially parallel alignment with an axis parallel to the long dimension of the elongate probe.

In preferred embodiments of the present invention in which the structure includes arms that protrude from the elongate probe through openings in its outer surface, the probe preferably further includes one or more lumens, and the structure has a second configuration in which the arms are held inside the one or more lumens.

Preferred embodiments of the present invention further provide that at least one of the one or more position signal generating devices is fixed in a known relation to the position of the structure in its substantially rigid configuration. Preferably at least one of the one or more position signal generating devices is fixed to the distal end of the elongate probe.

Preferably the position signal generating device comprises one or more coils, which generate position signals in response to an externally applied magnetic field. Preferably at least one of the coils is coaxial with an axis defined by the long dimension of the elongate probe.

Preferably at least one of the one or more position signal generating devices generates six-dimensional position and orientation information. Alternatively, the one or more position signal generating devices include at least two devices for generating three-dimensional location information, placed in a mutually spaced relation. One of the one or more position information generating devices may be associated with each of the sensors.

Alternatively, the one or more position signal generating devices may include at least one device that generates three-dimensional location signals, and at least one device that generates angular orientation signals. Preferably, the at least one device that generates angular orientation signals is a rotation measuring device. This rotation measuring device may generates information regarding the rotation of the catheter about an axis defined by the catheter's long dimension. Alternatively or additionally, the device may generate information regarding deflection of the distal end of the catheter.

Preferred embodiments of the present invention provide that the sensors be adapted to detect electrical impulses in the endocardium, where, preferably, the sensors are electrodes adapted to be placed in contact with the endocardium.

Alternatively, the sensors may be adapted to detect electrical signals in the brain, or the sensors may be ionic sensors.

Preferred embodiments of the present invention further include signal processing circuitry, which receives and processes position signals from the probe, so as to determine the positions of the physiological sensors. This signal processing circuitry is preferably further or alternatively adapted to measure a vector relating to the physiological activity.

There is further provided in accordance with a preferred embodiment of the present invention, apparatus for measuring physiological activity, including an elongate probe for insertion into the body of a subject, which probe includes a plurality of physiological sensors, which generate signals responsive to the physiological activity; and signal processing circuitry, which receives and processes physiological signals from the probe, so as to measure a vector relating to the physiological activity.

In accordance with a further preferred embodiment of the present invention, there is provided apparatus for measuring physiological activity including elongate probe apparatus adapted to detect electrical impulses in the endocardium, as described above, and further including signal processing circuitry, which measures an electrical activation vector in the heart.

Furthermore, in accordance with other preferred embodiments of the present invention, there is provided apparatus including a first elongate probe adapted to detect electrical impulses in the endocardium, as described above; and a second elongate probe, having a distal end, which is inserted into a human body, and a device that generates position signals indicative of the three-dimensional location of the distal end of the second probe. Preferably, the second elongate probe is adapted to be substantially fixed in a chamber of the heart, and the position signals generated by the device indicative of the location of the distal end of the second probe define a reference frame relative to which the position and orientation of the structure of the first elongate probe are determined. Preferably the second probe is adapted to be substantially fixed adjacent to the apex of the heart.

There is further provided in accordance with a preferred embodiment of the present invention, a method for mapping electrical activity in the endocardium of a heart, including:

inserting a catheter, having a distal end, to which a structure having a substantially rigid configuration is connected, and to which structure a plurality of sensors are fixed in known positions, into a chamber of the heart, so as to bring the sensors into contact with a locus in the endocardium;

receiving electrical signals indicative of electrical activity in the endocardium at the plurality of sensors;

determining the respective position of the sensors using position information generated by one or more position information generating devices fixed in known relation to the sensors.

Moreover, there is provided in accordance with another preferred embodiment of the present invention, a method for mapping electrical activity in the endocardium of a heart, including:

inserting a first catheter, having a distal end, to which a structure having a substantially rigid configuration is connected, and to which structure a plurality of sensors are fixed in known positions, into a chamber of the heart, so as to bring the sensors into contact with a locus in the endocardium;

inserting a second catheter, having a distal end, to which a device that generates three-dimensional location information is connected, into a chamber of the heart, so as to fix the distal end of the second catheter in a known, predetermined position in the chamber of the heart;

receiving electrical signals indicative of electrical activity in the endocardium at the plurality of sensors;

determining the respective positions of the sensors relative to a reference frame defined by the second catheter, using position information generated by one or more position information generating devices fixed in known relation to the sensors.

Preferably, in either of the above methods, the structure is inserted into a chamber of the heart by passing the structure through a blood vessel, and during insertion, the structure assumes a second configuration, which is narrow and elongated so as to pass easily through the blood vessel.

Preferably the electrical signals and the position information in accordance with the above methods are used to determine an activation vector at the locus. Preferably the vector is determined by measuring activation times of the electrical signals.

Furthermore, the one or more devices for generating position information preferably measure the position and orientation of the structure.

Preferred embodiments of the present invention provide that the sensors are coupled together as bipolar electrodes, and the vector is determined by measuring amplitudes of electrical signals received from the bipolar electrodes.

Preferred embodiments of the present invention further provide that the activation vector is mapped by receiving electrical signals from the endocardium and determining the respective positions of the sensors at multiple loci in the heart. Preferably the location of a defect in the heart's electrical conduction is determined by measuring the direction of propagation of electrical impulses in the heart repeatedly at multiple locations.

There is further provided, in accordance with a preferred embodiment of the invention a catheter insertable into a body vessel comprising: a tubular body portion; at least one resilient member extending from a distal end of said tubular body portion, said at least one resilient member being adapted to bend over the outside of the distal end of the tubular portion and to extend distally from the distal end of the tubular portion.

Preferably, the at least one resilient member is adapted to bend over the outside of the distal end of the tubular portion during distal motion of the catheter in a vessel and is adapted to extend distally from the distal end of the tubular portion during proximal motion of the catheter in the vessel.

In a preferred embodiment of the invention the at least one resilient member has a rest position at which it does not extend axially from the tubular section.

In a preferred embodiment of the invention, the at least one resilient member comprises a plurality of resilient members attached to the distal end of the tubular section. Preferably the plurality of resilient members are substantially symmetrically arranged about a longitudinal axis of said catheter.

In a preferred embodiment of the invention the at least one resilient member is comprised in a cap attached to the distal end of the tubular member. Preferably, the cap comprises a sleeve extending from a proximal end of said resilient member and attachable to said distal end of said tubular body portion, wherein at least one radial dimple is formed at a juncture between said sleeve and said resilient member.

In a preferred embodiment of the invention the at least one resilient member is constructed of an elastomeric material.

Preferably the catheter comprises at least one bump protruding from said at least one resilient member, preferably having at least one sensor fixed to said bump.

Preferably the catheter comprises at least one sensor fixed to said at least one resilient member.

In preferred embodiments of the invention the at least one sensor is selected from the group consisting of a position sensor, a six degree of freedom position and orientation sensor, a monopolar electrode, a bipolar electrode, a strain gauge and a physiological activity sensor.

There is further provided, in accordance with a preferred embodiment of the invention, a method for sensing a physiological activity of tissue inside a body organ, comprising:

inserting a catheter having at least according to any of claims 72–74 into said body organ;

sensing a physiological activity of said tissue with each sensor.

Preferably the sensors sense a physiological activity substantially simultaneously.

In preferred embodiments of the invention the physiological activity is selected from the group consisting of movement of said tissue, contraction time of a heart muscle, an activation signal of a heart muscle, and velocity of fluid flow.

There is further provided, in accordance with a preferred embodiment of the invention, a method for determining a velocity relating to physiological activity at a location in a tissue, comprising:

receiving signals indicative of physiological activity at a plurality of known positions adjacent to the location in the physiological tissue;

measuring a respective characteristic time at each of the plurality of positions using the signals received therefrom;

computing velocity component vectors along two non-parallel axes, wherein the velocity component vectors are defined by the known positions and the measured activation times; and applying vector arithmetic operations to the velocity component vectors to determine the velocity at the location.

In a preferred embodiment of the invention each of the two non-parallel axes is defined by a respective pair of the known positions. Preferably each of the velocity component vectors has a magnitude determined by arithmetically dividing the distance separating the pair of known positions that define the respective axis of the velocity component vector, by the difference of the characteristic times between the known positions.

In a preferred embodiment of the invention and including finding one of the plurality of positions that has a characteristic time not substantially equal to the characteristic times of the other positions. Preferably the method comprises taking the position whose characteristic time is not substantially equal to the characteristic times of the other positions as a reference point for computing the velocity component vectors. Preferably, both of the non-parallel axes are taken to pass through the reference point.

In a preferred embodiment of the invention the method includes the location as a possible site of pathology when all of the plurality of positions are found to have a substantially equal characteristic times.

Preferably, the method includes determining the coordinates of the location relative to an external frame of reference.

In a preferred embodiment of the invention, where the signals are electrical signals, which are received by a plurality of electrodes at a plurality of known, respective positions.

Preferably, the method comprises fixing the electrodes at the distal end of a catheter, and inserting the catheter into a chamber of the heart of a subject, and wherein the velocity is a velocity of local electrical activation in the endocardium. Preferably, the method bringing the electrodes into contact with the endocardium, adjacent to the location at which the velocity is to be determined. In a preferred embodiment of the invention, the velocity is a measure of ionic current.

In a preferred embodiment of the invention the method comprises bringing the electrodes into proximity with a location in the brain, and wherein the velocity is a velocity of local electrical activation in the brain of a subject.

In accordance with a preferred embodiment of the invention, there is further provided a method of mapping the velocity of local electrical activation in a plurality of locations in the endocardium, comprising determining the velocity at a plurality of known locations in the tissue, in accordance with the above described method, and recording the velocity thus determined as a function of the respective known locations.

BRIEF DESCRIPTION OF THE DRAWINGS

The present invention will be more fully understood from the following detailed description of the preferred embodiments thereof, taken together with the drawings in which:

FIG. 4A is a schematic, perspective representation of a system including a catheter, to which electrodes are fixed, according to a preferred embodiment of the present invention;

DETAILED DESCRIPTION OF PREFERRED EMBODIMENTS

Figure 1:
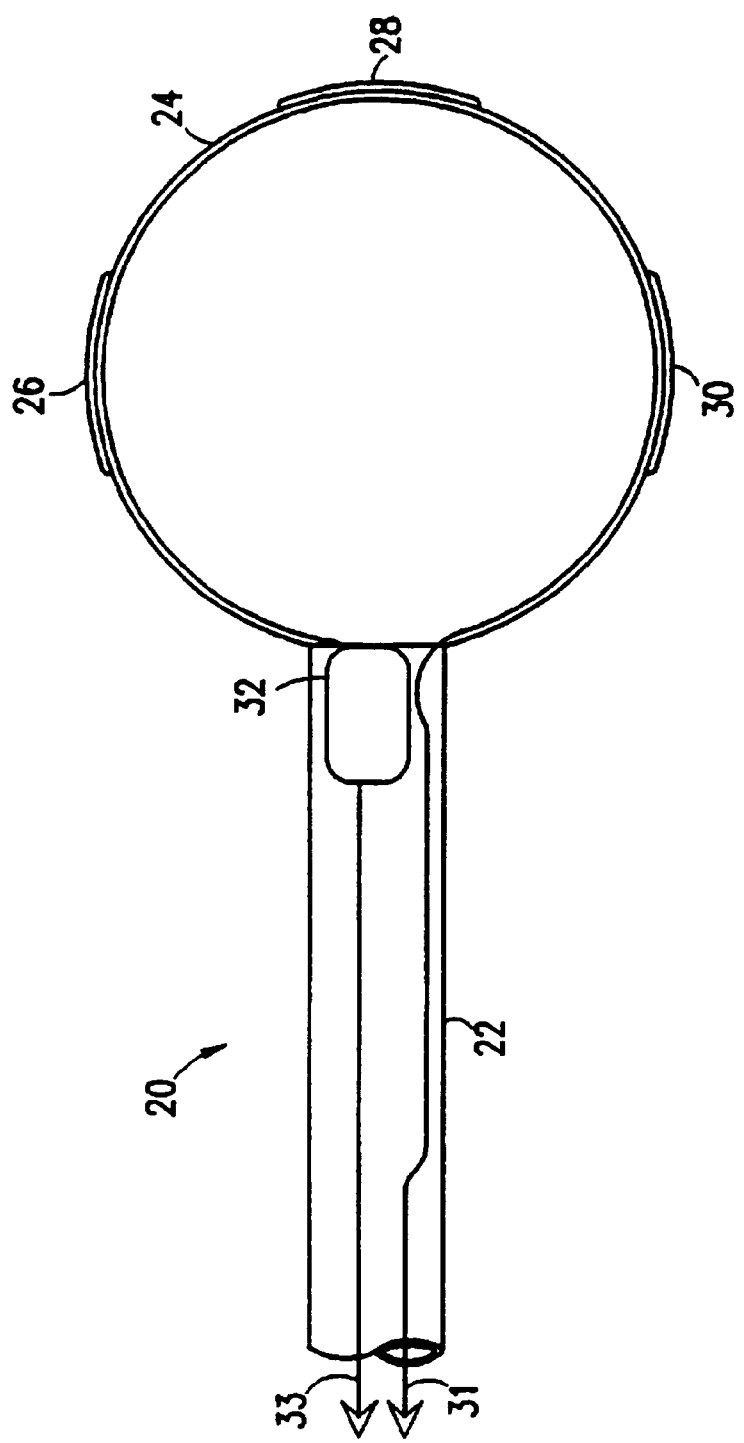
FIG. 1 is a generalized, conceptual schematic illustration of a catheter, in accordance with a preferred embodiment of the present invention.

Reference is now made to FIG. 1, which is a conceptual, schematic illustration of the distal end of a catheter 20 in accordance with a preferred embodiment of the present invention. The catheter comprises an outer sheath or sleeve 22 and a substantially rigid ring 24 at the catheter's distal end. A plurality of sensor electrodes 26, 28, 30 are fixed to ring 24 in such manner that when the ring is placed against a biological tissue, such as the endocardium, the electrodes receive electrical signals from the tissue. These signals are conveyed by conducting wires 31 inside sheath 22 to signal processing electronics, not shown in the drawings.

Various modes of construction of electrodes 26, 28, 30, and signal processing electronics for electrophysiological measurements in the heart are known in the art and do not form, per se, a part of the present invention. The present invention may be used with any of these modes, as appropriate for the measurement being performed.

It will further be appreciated that while three electrodes are shown in the schematic illustration of FIG. 1, in preferred embodiments of the invention larger numbers of electrodes may be attached to ring 24, so as to enhance the accuracy of the electrophysiological measurements. In other preferred embodiments of the present invention, ring 24 or another structure at the distal end of catheter 20 may comprise only two electrodes. The two electrodes may be successively repositioned about a location in the tissue so as to make multiple successive measurements, which are collectively used for determining the direction of a vector at the location.

As will be explained in the discussion that follows, the three electrodes 26, 28 and 30, as shown in FIG. 1, are sufficient for determining the direction of a velocity vector in the biological tissue with which they are in contact, in accordance with preferred embodiments of the present invention. In other preferred embodiments of the present invention, however, larger numbers of electrodes may be attached to ring 24. In such embodiments, the additional data provided by the greater number of electrodes may be used to determine the vector with greater accuracy, or to resolve anomalous measurements due to pathologies in the tissue, for example.

Catheter 20 further comprises a device 32 for generating six-dimensional position and orientation coordinate information. Coordinate information device 32 provides electrical signals via conducting wires 33 to signal processing electronics (not shown in the drawings), which determine the six coordinates of translational position and angular orientation of device 32 relative to an external frame of reference. In preferred embodiments of the present invention wherein catheter 20 is flexible, coordinate information device 32 is attached to ring 24 or is placed adjacent to the distal end of the catheter in a fixed, known relation to ring 24, so that the position and orientation of ring 24 are known relative to device 32. In other preferred embodiments using rigid catheters, for use in neurosurgery, for example, the coordinate information device may be located at any point along the length of the catheter, although it is preferably located near the distal end.

In the context of this invention, the term substantially rigid, as applied to ring 24 at the distal end of catheter 20, is taken to mean that during successive measurements of electrophysiological signals by the electrodes, the shape of the ring and its angular orientation relative to coordinate information device 32 remain substantially unchanged. Consequently, the location of each of the electrodes on the ring relative to coordinate information device 32 is substantially constant, and thus the locations of all the electrodes relative to an external reference frame may be determined using the location and orientation information provided by the coordinate information device. During insertion and removal of the catheter from the body, however, this relationship may not be preserved.

Figure 2:
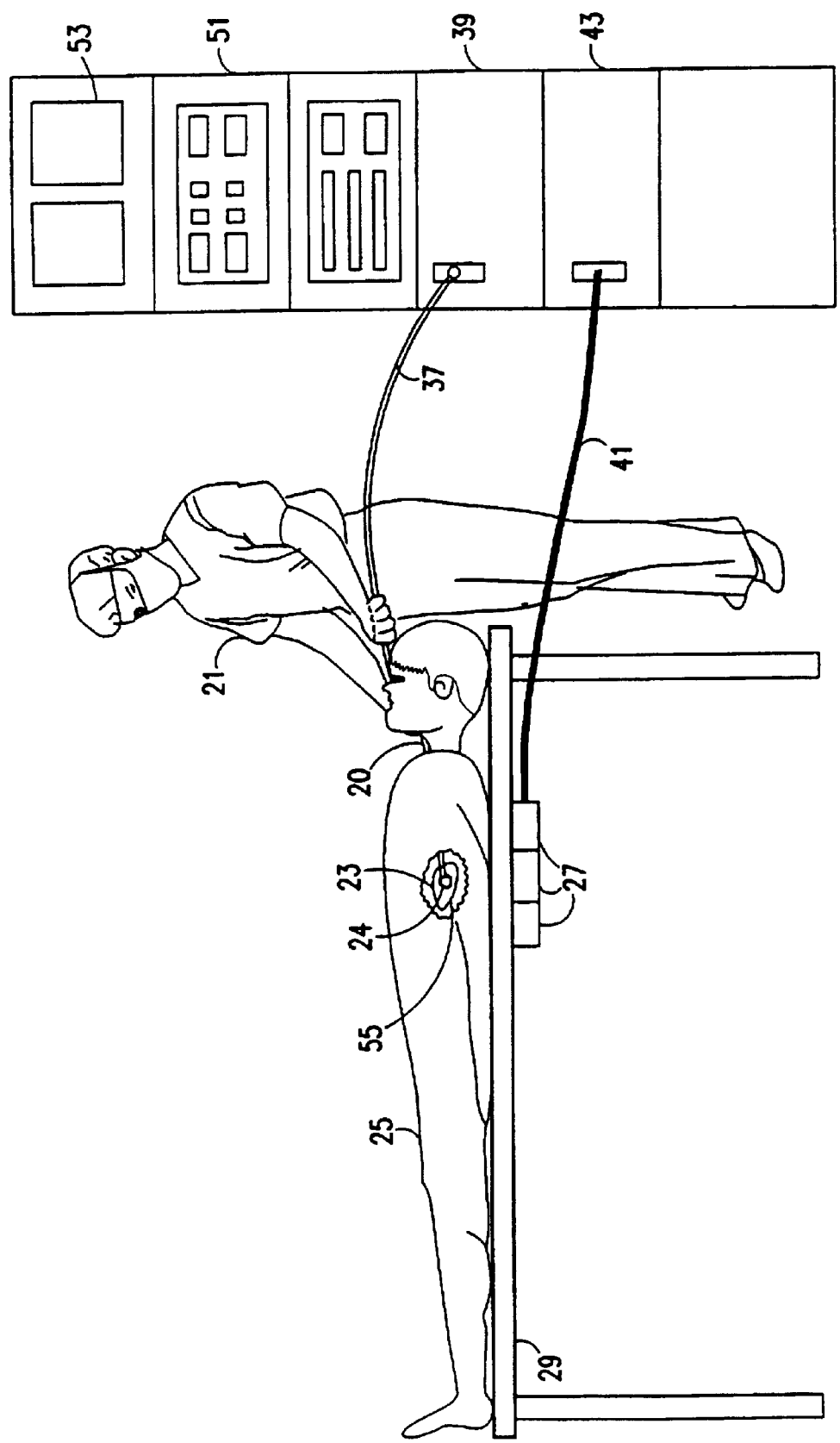
FIG. 2 is a schematic illustration of a system incorporating the catheter of FIG. 1, in accordance with a preferred embodiment of the present invention.

In preferred embodiments of the present invention, catheter 20 is used as part of a system for mapping physiological activity, as illustrated schematically in FIG. 2. A surgeon 21 inserts catheter 20 through an incision into a chamber of heart 23 of a patient 25, so that ring 24 with its associated electrodes (not shown in FIG. 2) and coordinate information generating device 32 are inside the chamber. In accordance with an exemplary position determination device described in PCT patent application number PCT/US95/01103, filed Jan. 24, 1995, and U.S. Pat. No. 5,391,199, which are assigned to the assignee of the present application and whose disclosures are incorporated herein by reference, device 32 generates position signals in response to externally applied magnetic fields, generated by electromagnetic field generator coils 27, which are fixed to the operating table 29. Catheter 20 is connected at its proximal end via a cable 37, which contains conducting wires 31 and 33 (shown in FIG. 1), to signal processing electronic circuits 39. Field generator coils 27 are similarly connected via cable 41 to driver circuits 43. Circuits 39 and 43 are connected to a computer 51, which controls their operation and receives signals therefrom, and which is also coupled to monitor screen 53.

To map electrical activity in heart 23, surgeon 21 operates catheter 20 so as to bring ring 24 to bear against a point on the endocardium 55. Circuits 39 receive and process position signals generated by device 32 and electrical signals received by electrodes 26, 28 and 30 (shown in FIG. 1), and convey these signals to computer 51. The computer uses the processed signals to determine the locations of electrodes 26, 28 and 30 and to compute a local electrical activation vector 38, as will be described below with reference to FIG. 3. The surgeon operates the catheter so as to move the ring to multiple other points on the endocardium, repeating the above steps at each such point. The computer uses the signals received at the multiple points to generate a map of vector 38, which is displayed, along with other useful data, on monitor screen 53. The map may also be stored and recorded for later use, by means and methods known in the art.

Preferably, measurements by coordinate information device 32 are substantially synchronized with the heart cycle, with all measurements made during diastole, for example, so as to eliminate errors, that may arise in determining positions of electrodes 26, 28 and 30, due to movement of the heart. The electrodes, however, remain fixed in their positions adjacent to the endocardium during all parts of the heart cycle, until the surgeon moves them.

Figure 3:
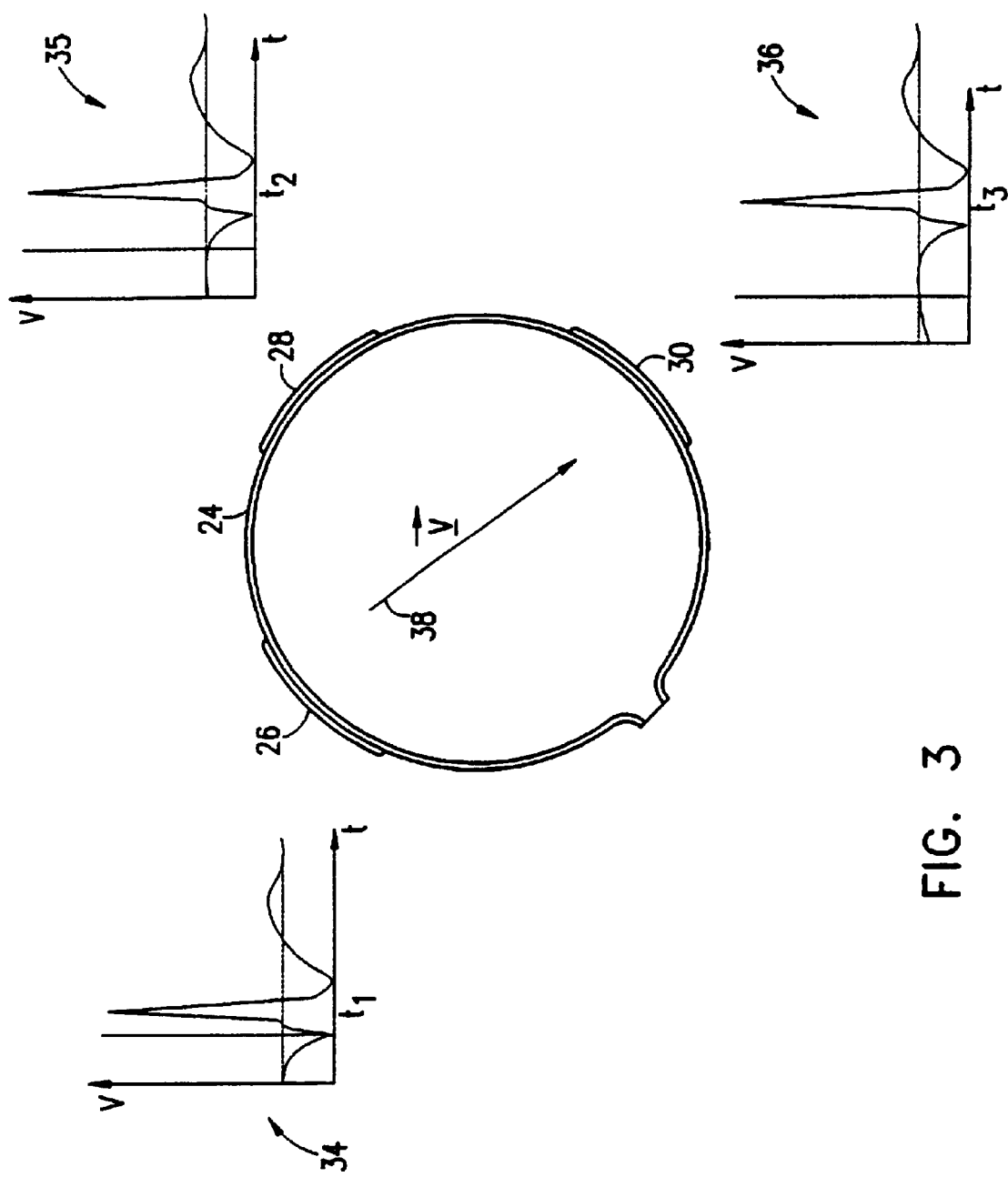
FIG. 3 is a schematic representation of a portion of the catheter of FIG. 1, showing electrical signals as received at different sites thereon, useful in understanding the operation of the invention.

The operation of the present invention will be better understood by reference to FIG. 3, which shows ring 24 and electrodes 26, 28, 30 thereon, together with representations of electrograph signals 34, 35, 36 that are typically received from electrodes 26, 28, 30, respectively, when the ring is positioned so that the electrodes are in contact with the endocardium. Signals 34, 35 and 36 are shown schematically for explanatory purposes only. For the signals shown, vector $\vec{V}$ 38 represents the direction of an electrical activation vector in the endocardium at the location of the ring.

As indicated by the direction of vector $\vec{V}$, the sharp electrical impulse peak shown in graphs 34, 35 and 36 will reach electrode 26 first, at time $t_1$, and subsequently electrode 28, at time $t_2$, and finally, electrode 30, at time $t_3$. Typically such a sharp electrographic impulse peak, which is seen in the well-known QRS portion of the electrocardiogram waveform, propagates through the heart muscle to induce contraction.

The relative time of arrival of the signal peak at each of the electrodes can thus be used to determine the magnitude and direction of $\vec{V}$ relative to ring 24. Referring to FIG. 3, we note by way of example that the time difference between the signal peaks at electrodes 26 and 28, $\tau_2=t_2-t_1$, is roughly twice the time difference for electrodes 26 and 30, $\tau_3=t_3-t_1$. This temporal measurement indicates that the electrical activation wave front passing electrode 26 takes twice as long to reach electrode 30 as it does to reach electrode 28, and thus that vector $\vec{V}$ points from the position of electrode 26 toward that of electrode 30. If the ratio $\tau_2/\tau_3$ were relatively smaller, $\vec{V}$ would be found to be rotated clockwise relative to the direction shown in FIG. 3, while if the ratio were larger, $\vec{V}$ would be rotated counterclockwise.

Although the above example and preferred embodiments of the present invention described herein refer specifically to three electrodes and signals received therefrom, it will be understood that preferred embodiments of the present invention may comprise four or more electrodes. The additional arrival time data provided by the larger number of electrodes may be used to determine the direction of $\vec{V}$ with greater accuracy.

Other preferred embodiments of the present invention may include only two electrodes, in which case a single measurement will give a general indication of the direction of $\vec{V}$, and multiple, sequential measurements may be used to determine the direction of $\vec{V}$ with greater accuracy. It is generally preferable, however, that the distal end of the catheter comprise at least three non-collinear electrodes, so that the vector $\vec{V}$ may be fully determined as shown in FIG. 3.

Although in FIG. 3 the amplitudes of signals 34, 35 and 36 are all roughly the same, at certain locations in the endocardium, and particularly in the vicinity of pathological areas of the heart, the relative amplitudes of the signals may vary, and these amplitude variations may also be useful in locating and diagnosing the pathology.

For example, pairs of electrodes, such as electrodes 26 and 28, may be coupled together so as to act as bipolar electrodes. In this case, the signal processing electronics will detect the electrical potential difference between electrodes 26 and 28, for example, corresponding substantially to the local electrical activity between the electrodes. If, in this example, the direction of the local electrical activation vector $\vec{V}$ has a large component directed from electrode 26 toward electrode 28, the bipolar signal measured between these electrodes will have relatively large amplitude. If the vector has a large component directed from electrode 28 toward electrode 26, the bipolar signal will also have relatively large amplitude, although of opposite sign to that of the preceding case. If, however, the vector points in a direction substantially perpendicular to an axis passing through electrodes 26 and 28, the amplitude of the bipolar signal will be relatively small or zero.

It will be understood that any direction of the vector $\vec{V}$ can be decomposed into components parallel and perpendicular to an axis passing through a pair of electrodes, and the amplitude of the bipolar signal between these electrodes will be proportional to the relative magnitude of the parallel component. Thus, by integrating the area under the bipolar signal peak with respect to time, and comparing the integrated signals obtained from two or more electrode pairs, the direction of the local electrical activation vector $\vec{V}$ can be determined using the relative amplitudes rather than the arrival times of the signal peaks.

Since the position and orientation of ring 24, relative to the distal end of catheter 20 and coordinate information device 32, are known, the direction of vector $\vec{V}$ can be determined relative to the external frame of reference. This external frame of reference is preferably substantially fixed in relation to the heart muscle, using methods that will be discussed in greater detail below. By moving the distal end of the catheter from location to location inside the heart and repeating the measurement of signals 34, 35, 36, a map of $\vec{V}$ as a function of position on the surface of the endocardium may be conveniently generated.

Figure 4B:
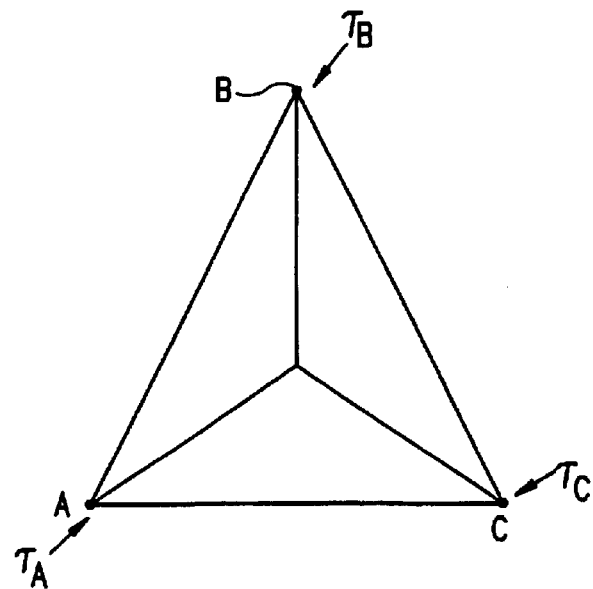
FIGS. 4B–D are schematic drawings showings steps of calculating a conduction velocity in accordance with a preferred embodiment of the invention.
Figure 4C:
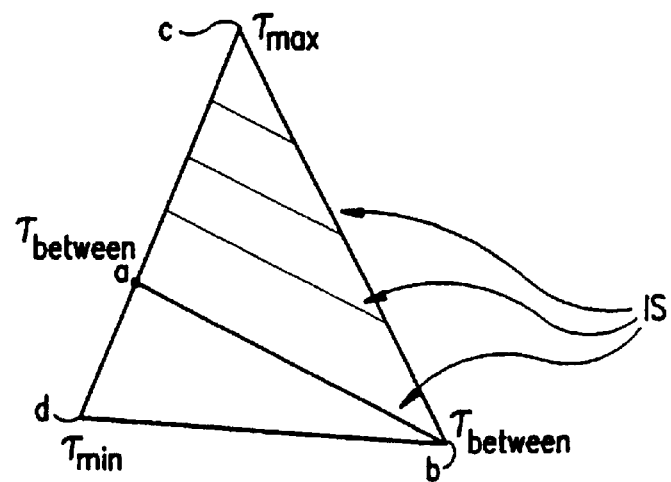

Another method of conduction velocity determination, in accordance with a preferred embodiment of the invention, calculates the velocity vector as being perpendicular to local isochronals of an activation front (marked as IS in FIG. 4C). FIG. 4A shows a structure 240 at the distal end of a catheter 220, which is similar to the structure of FIGS. 10A–10C. Structure 240 at the distal end of catheter 20, comprises a plurality of arms 242 to which electrodes 226, 228 and 230 are fixed in known relative positions. Preferably the electrodes are placed into contact with the endocardium of the heart of a subject, and generate local electrogram signals in response to electrical potentials in the endocardium. These signals are preferably conveyed through arms 242 and catheter 220 to signal processing apparatus 248, which processes the signals to determine a local activation time at the respective position of each of the electrodes.

It will be understood that while catheter 220 is useful in conjunction with preferred embodiments of the present invention, it is shown in FIG. 4A only by way of illustration, for clarity in describing a method of velocity determination, in accordance with preferred embodiments of the present invention. The method of the present invention as described below may similarly be used in conjunction with other types of structures that allow for placement of electrodes at known, spaced positions in contact with physiological tissue, such as those described herein.

A Cartesian coordinate frame 244 is defined by the positions of the catheter and the electrodes, wherein the Z-axis is aligned with the long axis of catheter 220, the Y-axis is defined by a line normal to the Z-axis and passing through electrode 226, and the X-axis is perpendicular to both the Y- and the Z-axes. The positions of electrodes 226, 228 and 230 are marked respectively as A, B and C in the figure in coordinate system 244, for clarity in the explanation that follows.

As shown in FIG. 4A, position- and orientation-responsive signals generated by device 232 are conveyed to position sensing apparatus 246, which uses the signals to compute position and orientation coordinates of the catheter relative to a reference frame 250, comprising K, L and M axes as shown in FIG. 4A, defined by external radiator coils 27, which generate the magnetic fields.

Preferably, the position of the origin and the orientation of frame 244 are calibrated in relation to frame 250, before beginning to measure and map the electrical activation time. To perform this calibration, the distal portion of catheter 220 is placed in a known location and oriented so that each of the X, Y and Z axes of coordinate frame 244 is substantially aligned with one of the K, L and M axis of coordinate frame 250. The position and orientation coordinates of catheter 220 at this location and orientation, as computed by position sensing apparatus 246, are then recorded and used subsequently as zero-reference points in computing position and orientation coordinates of the catheter during measurement and mapping. Preferably, at least one of the electrodes is selected as the reference electrode and is aligned with one of axes K, L or M. Alternatively, to using frame 250, a local reference frame, such as one coupled to the heart may be used, as described herein.

Figure 4D:
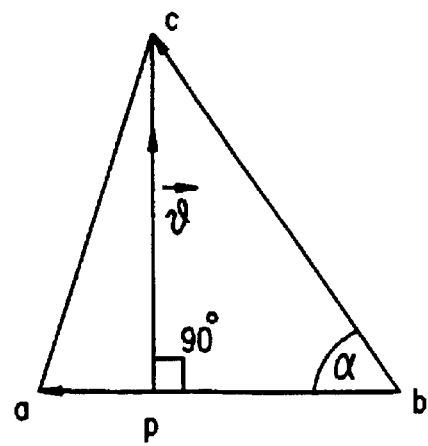
Figure 5:
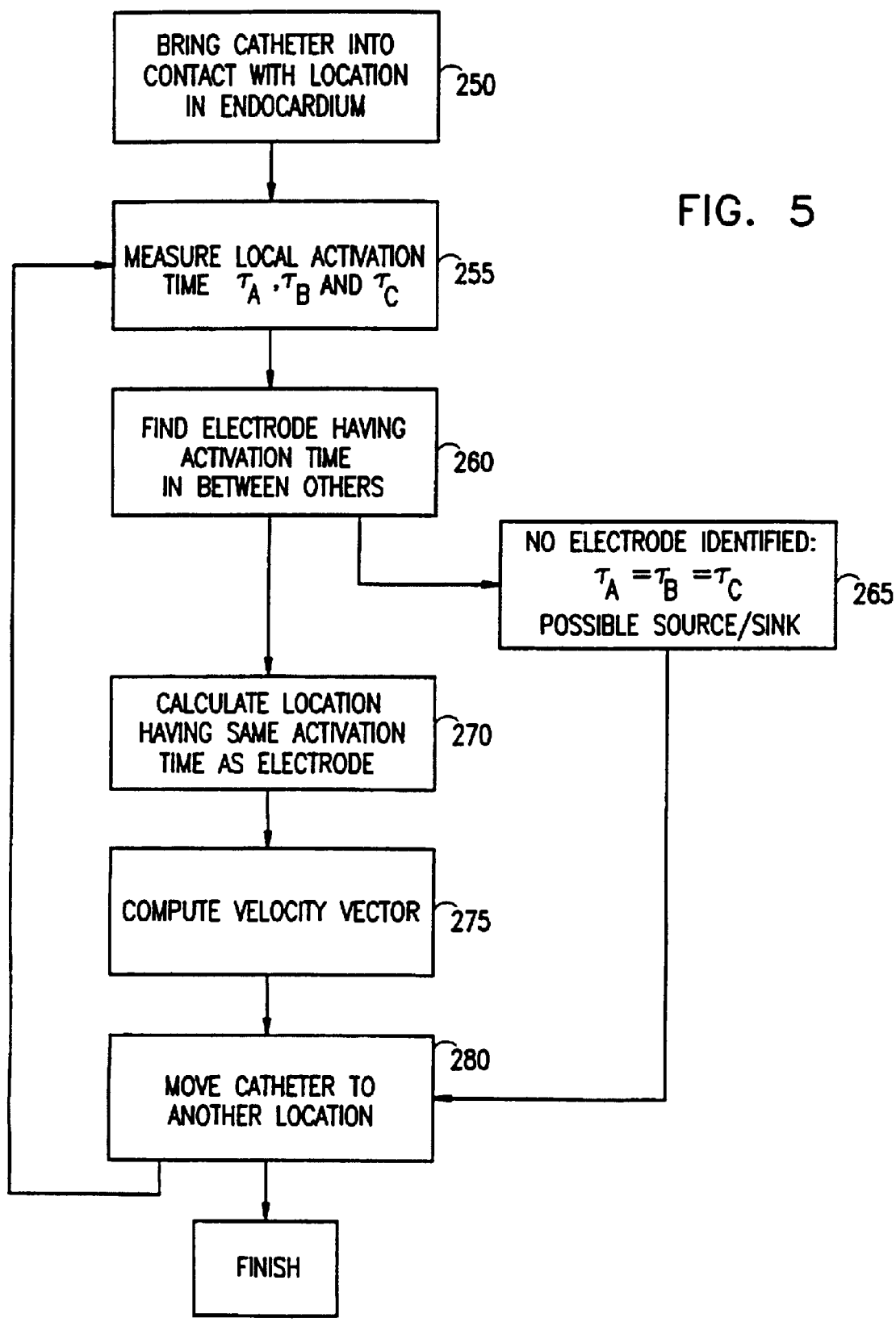
FIG. 5 is a flow chart illustrating schematically a method of determining the magnitude and direction of a vector, in accordance with a preferred embodiment of the present invention, as shown in FIGS. 4B–D.

FIGS. 4B–D and 5 illustrate a method, in accordance with preferred embodiments of the present invention, for mapping a vector velocity of electrical activation $\vec{V}$, as a function of time, in the endocardium, using catheter 20 or similar apparatus. FIG. 5 is a flowchart of the method, while FIGS. 4B–D illustrate the method on a schematic of electrodes 226, 228 and 230. First, the catheter is brought into contact with a location in the endocardium, and positions A, B and C are determined, corresponding to the respective positions of electrodes 226, 228 and 230 and to respective portions of the endocardium. It will be appreciated that, in accordance with preferred embodiments of the present invention described herein, it is sufficient to determine the position and orientation of distal end of catheter 20, in order to determine A, B and C.

Next, local electrical activation times, $\tau_A$, $\tau_B$ and $\tau_C$, respectively, are measured by signal processing apparatus 48 at the respective positions of the electrodes. Measurement of electrical activation time is performed according to methods known in the art, for example by sensing sharp peaks in the electrogram signals received from the electrodes and determining thereby the relative time at which the local tissue depolarizes, as described above in reference to FIG. 3.

The depolarization time can be determined using bipolar electrodes, for example, by coupling together pairs of electrodes, such as electrodes 226 and 228, so as to act as bipolar electrodes. In this case, the signal processing electronics will detect the electrical potential difference between electrodes 226 and 228, for example, corresponding substantially to the local electrical activity between the electrodes. If, in this example, the direction of the local velocity vector $\vec{V}$ has a large component directed from electrode 26 toward electrode 28, the bipolar signal measured between these electrodes will have relatively large amplitude.

In a preferred embodiment of the invention, each of electrodes 226, 228 and 230 is a bipolar electrode comprised of two individual electrodes).

The local electrical activation times are compared so as to identify one of electrodes 226, 228 and 230 whose local electrical activation time is not equal to those of the other two electrodes. If such an electrode cannot be found, i.e., the local activation times of all three electrodes are equal or cannot be measured, then the local activation velocity $\vec{V}$ is determined to be zero, and the location in the endocardium with which the catheter is in contact is identified as a suspected site of pathology, for example a source or sink of electrical activation. In a preferred embodiment of the invention, catheter 220 is preferably moved to a new location on the endocardium, which location is a short distance from the previous location, such that there is substantial overlap in the endocardium which is mapped in the new location and in the previous location. Thus, it is possible to identify whether the previous location is a source, a sink, or possibly, dead scar tissue. It should be appreciated, that such precise relocalization is made possible using position sensing device 232.

In another preferred embodiment of the invention, a velocity map is repeated after a medical procedure, such as surgery or an ablation (even of a single point) and/or after a different pacing scheme is sued. Thus, the effect of such procedures on the conduction velocity is easily determined. Such temporally repeated mappings can be used to assess the advance of arrhythmias, as one effect of abnormal conduction is that the conduction velocity changes with time. In addition, the vector of the depolarization potential changes during the cardiac cycle. Measuring this vector, even at a single location in the heart, can provide much information regarding the functioning of the heart. If four non-coplanar electrodes are provided for in the catheter, the three-dimensional potential vector of the heart may be determined.

In the following discussion (FIGS. 4C and 4D), the electrode found to have the latest activation time, $\tau_{max}$, is marked "c", the electrode with the earliest activation time, $\tau_{min}$, is marked "d", and the electrode with the intermediate activation time, $\tau_{between}$, is marked "b".

A point "a" indicates a (calculated) location on the line connecting "c" and "d" which has the same activation time as electrode "b". The local isochronals are all assumed to be parallel to line "ab", which connects point "a" and point "b". Clearly, as the distance between electrodes 226, 228 and 230 decreases, the validity of this assumption increases, as does the precision of the method.

If two electrodes are found to have the same activation time (within an $\epsilon$), the local isochronals are assumed to be all parallel to the line connecting the two electrodes, and the velocity vector is perpendicular to the connecting line.

$\vec{V}$ is now computed, based on the following procedure, illustrated by FIG. 4C. Point "p" is located on the line "ab" connecting points "a" and "b", such that velocity vector $\vec{V}$ is perpendicular thereto. Using vector arithmetic:

$$\vec{Ab} = a - b \qquad (1)$$

$$\vec{Cb} = c - b \qquad (2)$$

$$\cos\alpha = \frac{\vec{Ab} \cdot \vec{Cb}}{\|\vec{Ab}\| \cdot \|\vec{Cb}\|} \qquad (3)$$

$$p - b = \|\vec{Cb}\| \cdot \cos\alpha \frac{\vec{Ab}}{\|\vec{Ab}\|} \qquad (4)$$

$$p = b + \|\vec{Cb}\| \cdot \cos\alpha \frac{\vec{Ab}}{\|\vec{Ab}\|} \qquad (5)$$

$$\vec{Cp} = c - p \qquad (6)$$

$$\vec{V} = \frac{\vec{Cp}}{\tau_{max} - \tau_{min}} \qquad (7)$$

In a vector based approach, A, B and C are vector coordinates of the electrodes (in reference frame 244 or 250) and are referred to as $\vec{A}$, $\vec{B}$ and $\vec{C}$.

A method, in accordance with preferred embodiments of the present invention, for mapping a vector velocity of electrical activation $\vec{V}$, as a function of time, in the endocardium, uses catheter 20 or similar apparatus. First, the catheter is brought into contact with a location in the endocardium, and vectors $\vec{A}$, $\vec{B}$ and $\vec{C}$, are determined, corresponding to the respective positions of electrodes 226, 228 and 230. It will be appreciated that in accordance with the preferred embodiment of the present invention described with reference to FIG. 4A, it is sufficient to determine the position and orientation of distal end of catheter 220, in order to determine $\vec{A}$, $\vec{B}$ and $\vec{C}$.

Next, local electrical activation times, $\tau_A$, $\tau_B$ and $\tau_{A'}$, respectively, are measured by signal processing apparatus 48 at the respective positions of the electrodes. Measurement of electrical activation time is performed according to methods known in the art, for example by sensing sharp peaks in the electrogram signals received from the electrodes and determining thereby the relative time at which the local tissue depolarizes, as described above in reference to FIG. 3.

Next, the local electrical activation times are compared so as to identify one of electrodes 226, 228 and 230 whose local electrical activation time is not equal to those of the other two electrodes. If such an electrode cannot be found, i.e., the local activation times of all three electrodes are equal or cannot be measured, then the local activation velocity $\vec{V}$ is determined to be zero, and the location in the endocardium with which the catheter is in contact is identified as a suspected site of pathology, for example a source or sink of electrical activation.

In the following discussion, we will assume that electrode 226 is found to have a local electrical activation time different from those of electrodes 228 and 230, and is thus taken as a reference point for determination of $\vec{V}$. It will be appreciated, however, that the method described below will be equally applicable if either electrode 228 or electrode 230 is thus found and taken as the reference.

$\vec{V}$ is now computed, based on the following procedure. Velocity component vectors $\vec{P}_B$ and $\vec{P}_C$ are determined based on the measured electrode positions and local electrical activation times:

$$\vec{P}_B = \frac{\vec{B} - \vec{A}}{\tau_B - \tau_A} \tag{8}$$

$$\vec{P}_C = \frac{\vec{C} - \vec{A}}{\tau_C - \tau_A} \tag{9}$$

$$\vec{P}_{CB} = \vec{P}_B - \vec{P}_C \tag{10}$$

$$\hat{P}_{CB} = \frac{\vec{P}_{CB}}{|\vec{P}_{CB}|} \tag{11}$$

$$\vec{V} = \vec{P}_B - (\hat{P}_{CB} \cdot \vec{P}_B)\hat{P}_{CB} \tag{12}$$

It will be appreciated from equation (10) that $\tau_B = \tau_C$, then $\vec{P}_{CB}$ will be normal to an axis passing through points B and C, which correspond to the positions of electrodes 224 and 226 respectively.

One advantage of using this second, vector based, method is its simplicity. Another advantage is that the electrode plane need not be perpendicular to the catheter. A further advantage is that the velocity is unambiguously determined. It should be noted that the determined velocity vector is in the coordinates of the heart, not of the catheter, since the transformation between the internal and external frames cancels out when the calculations of equations (8)–(12).

Catheter 20 is then moved to another location, and the procedure described above is repeated multiple times, so as to generate a map of $\vec{V}$ as a function of location in the endocardium. Preferably this map is used to determine locations of defects in the propagation of electrical activation in the endocardium, particularly to find sources and sinks of the activation. The map may further be compared with maps generated at earlier times, so as to identify changes in the local activation velocity over time.

In preferred embodiments of the present invention, ring 24 is made of resilient material. During insertion of the catheter through the patient's blood vessels and into the heart chamber, the ring is collapsed into an elongated shape so as to pass easily through the blood vessels. In the preferred embodiment shown schematically in FIG. 6A, during such insertion, the ring is contained inside catheter sheath 22. The ring is coupled to a stiff pushing member 40, which extends the entire length of the catheter. Position information device 32 is also coupled to pushing member 40, proximal to ring 24.

Figure 6A:
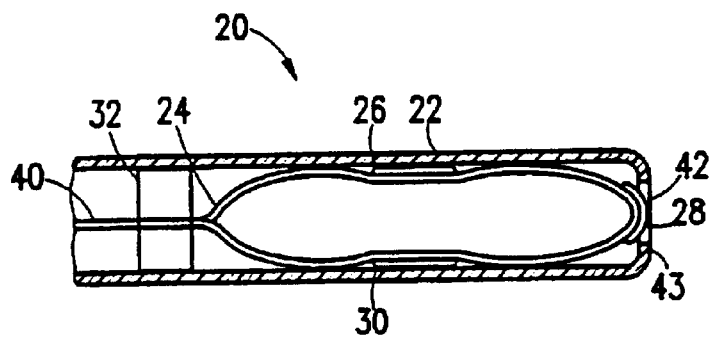
FIG. 6A is a cross-sectional view of a catheter in a configuration suitable for insertion into a patient's body and removal therefrom, in accordance with one preferred embodiment of the invention.
Figure 6B:
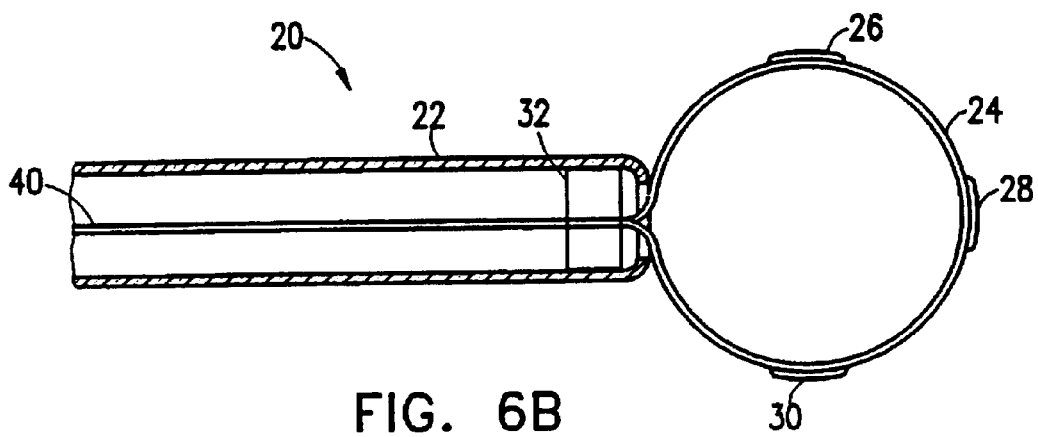
FIG. 6B is a cross-sectional view of the catheter of FIG. 6A in an alternative configuration suitable for performing electrophysiological measurements inside the body.

As shown in FIG. 6B, once the distal end of the catheter has been positioned inside the heart chamber, pressure is exerted on pushing member 40, and ring 24 is ejected through slot 42 in the surface 43 of the distal end of the catheter. The resilience of the ring then causes it to assume its desired, preferably circular, shape, which is brought into contact with surface 43. Position information device 32 simultaneously assumes its desired position adjacent to the distal end of catheter 20 inside sheath 22. Alternatively, coordinate information device 32 may be fixed in a constant position inside sheath 22, unaffected by the movement of pushing member 40.

Preferably ring 24 is formed from a resilient, super-elastic material, such as NiTi. Such materials have the property that when a piece of the material is heated above a certain critical temperature, it may be bent or formed into a desired shape. If the material held in this shape while it is cooled to below the critical temperature, then it will subsequently resiliently retain the given shape. Thus, although it may be compressed or bent by exertion of sufficient force, once the force is removed, the super-elastic material will return resiliently to its given shape, in this case a ring.

When the catheter is to be withdrawn from the heart, pushing member 40 is pulled back, thereby drawing ring 24 back through slot 42, reassuming the shape shown in FIG. 6A.

Figure 7:
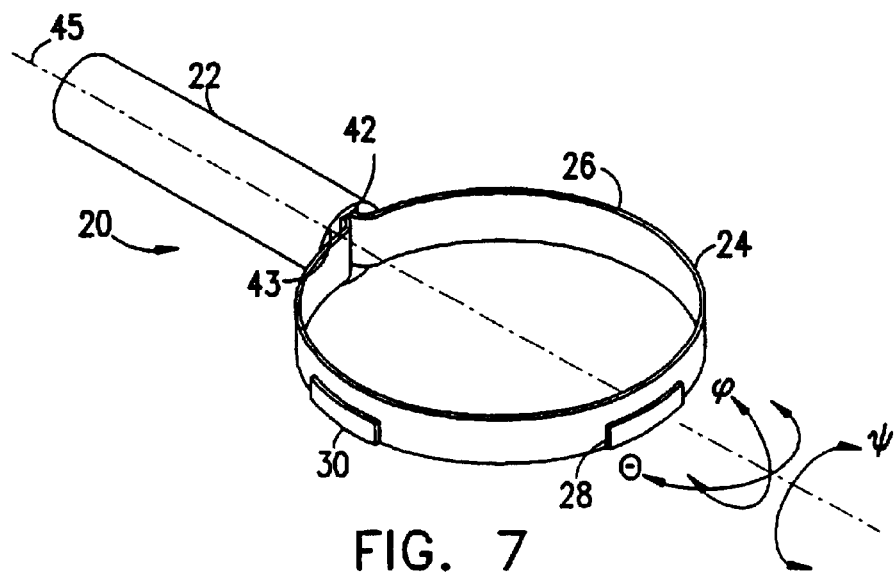
FIG. 7 is a three-dimensional graphic representation of the catheter shown in FIG. 6B.

As shown in FIG. 7, which is a perspective view of the preferred embodiment of FIGS. 6A and 6B, in a preferred embodiment of the present invention, ring 24 is formed from a flat strip of material, which is bent into a ring shape. Once the ring has been ejected from the catheter, its elasticity causes it to bear against the edges of slot 42, so as to hold the ring in a known angular orientation relative to the axis 45 of the catheter and prevent rotation in a direction, indicated by ψ, about axis 45, as shown in FIG. 7. The flat shape of the ring material effectively prevents the ring from tilting in an up-down direction, indicated by θ, relative to axis 45. The flat surface of the ring also bears against the flat surface 43 of the distal end of the catheter, thereby preventing wobble of the ring in a side-to-side direction, indicated by φ, relative to axis 45. Thus, since the geometrical shape and dimensions of ring 24 are known, and its angular orientation relative to catheter axis 45 is substantially fixed, the locations of electrodes on the ring can be determined from the six-dimensional position and orientation data provided by coordinate information device 32.

Preferably, electrodes 26, 28 and 30 extend to and, more preferably, extend below or around the lower edge of ring 24.

Figure 8A:
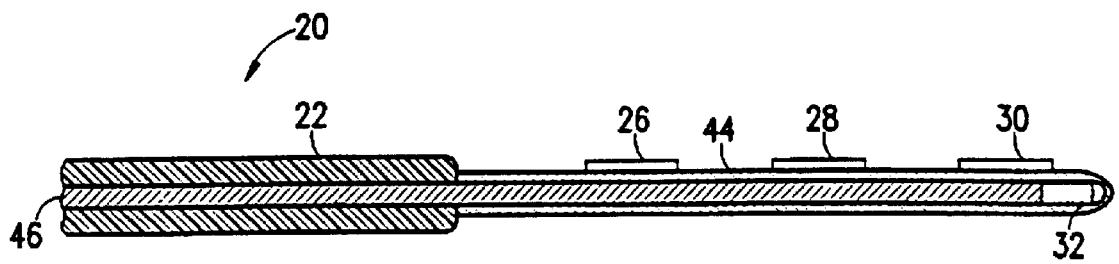
FIG. 8A is a cross-sectional view of a catheter in a configuration suitable for insertion into a patient's body and removal therefrom, in accordance with another preferred embodiment of the invention.
Figure 8B:
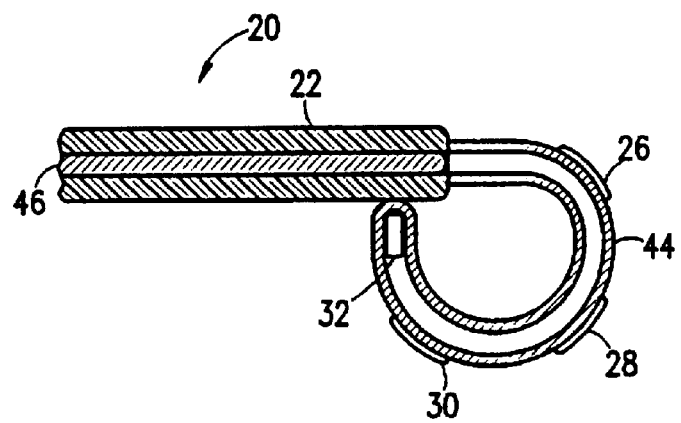
FIG. 8B is a cross-sectional view of the catheter of FIG. 8A in an alternative configuration suitable for performing electrophysiological measurements inside the body.

In another preferred embodiment of the present invention, shown in FIGS. 8A and 8B, electrodes 26, 28, 30 are attached to a ring 44 formed from a hollow section of substantially rigid material, such as a tube, which is closed off at its distal end. The ring is rigidly coupled to the distal end of catheter 20, so that its geometric shape and angular orientation relative to the axis of the catheter are known. Ring 44 also comprises coordinate information device 32 adjacent to its distal end. Alternatively, device 32 may be located in catheter 20.

When the catheter is to be inserted through the patient's blood vessels and into the heart, a stylette 46 is inserted from the proximal end of the catheter, through catheter sheath 22 and into the lumen of the tube from which ring 44 is formed, thereby straightening the ring as shown in FIG. 8A. Only the distal end of stylette 46 is substantially rigid, and the remaining length of the wire may be flexible, as long as it is stiff enough to allow it to be pushed into the hollow center of ring 44 for insertion and removal of the catheter from the heart.

Once the distal end of the catheter is inside the heart chamber, stylette 46 is withdrawn, and ring 44 resumes its predetermined circular shape and orientation, as shown in FIG. 8B.

Figure 8C:
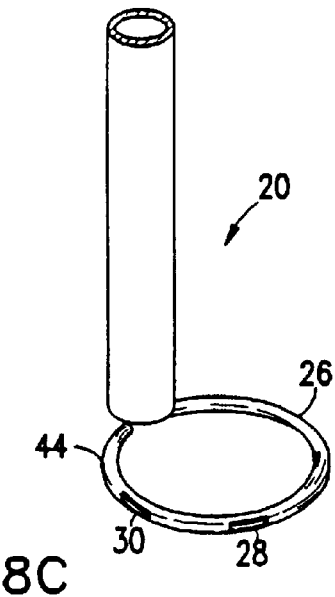
FIG. 8C is a perspective view of the catheter of FIG. 8A in a different alternative configuration suitable for performing electrophysiological measurements inside the body.
Figure 9:
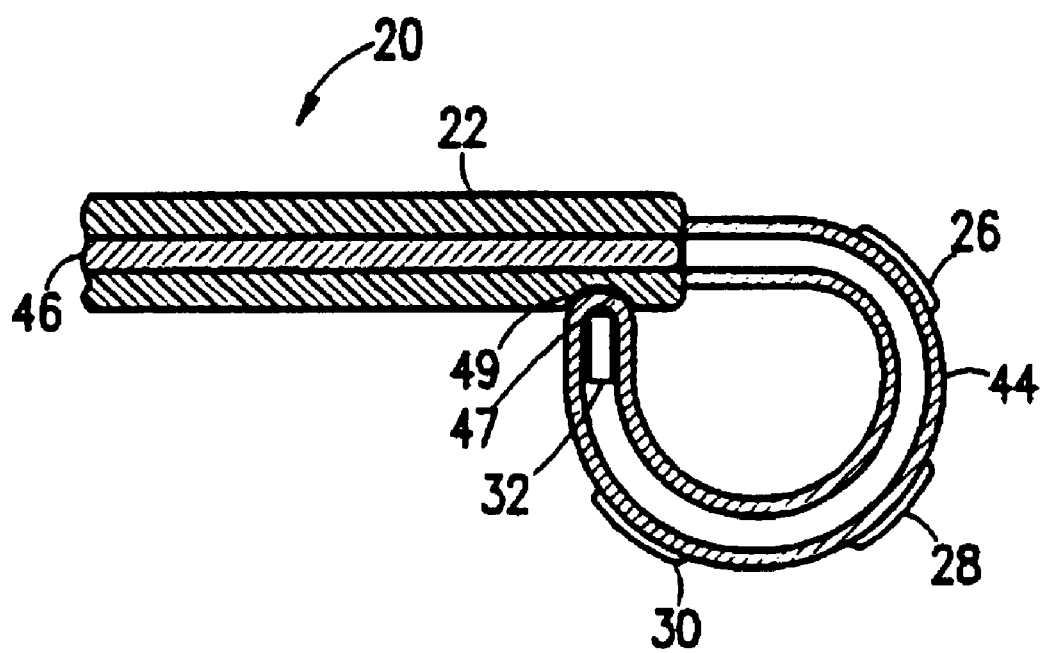
FIG. 9 is a cross-sectional view of a catheter in accordance with an alternative preferred embodiment of the invention, in a configuration suitable for performing electrophysiological measurements inside the body.

In another preferred embodiment of the present invention, shown in FIG. 8C, ring 44 is so formed that when stylette 46 is withdrawn, the ring twists sideways, so that the axis of the ring is substantially parallel to the long axis of catheter 20. In this twisted orientation of ring 44, electrodes 26 (not shown), 28 and 30 attached to the ring may more easily be brought into contact with the endocardium.

In yet another, similar preferred embodiment of the present invention, ring 44 at the distal end of the catheter is formed of a hollow section of flexible material. For insertion or removal of the catheter from the body, this hollow section is straightened by insertion of a straight stylette 46 into the lumen of the hollow section. After insertion of the catheter into the heart, the straight stylette is withdrawn, and a second stylette (not shown in the figures), formed of substantially rigid material and including a curved portion at its distal end, is inserted. For insertion of this second stylette through a lumen of the catheter, the curved distal portion of the stylette is straightened, and the relative stiffness of the catheter causes the stylette to remain straight as it is passed through the catheter. When this stylette reaches the hollow, flexible section 44 at the distal end of the catheter, however, the resilience of the stylette causes its distal portion to resume its curved shape, and thus causes the hollow, flexible section of the catheter to curve, as well, into the desired ring shape.

In some preferred embodiments of the present invention in which the distal end of the catheter is straightened during insertion into the heart, when the section at the distal end of catheter 20 is caused to curve into a ring 44 after insertion, as shown in FIG. 7, distal tip 47 of the ring section engages a socket 49 in the side of the catheter. Fluoroscopy or other methods of imaging known in the art may be used to observe ring 44 at the distal end of the catheter and verify that distal tip 47 of the distal section has engaged socket 49, so as to ensure that the ring has assumed its desired shape and orientation prior to beginning electrophysiological measurements.

Alternatively, in some preferred embodiments of this type, distal tip 47 of the distal section of the catheter comprises a first electrical contact, not shown in the figures, and socket 49 in the side of the catheter comprises a second electrical contact, likewise not shown. When distal tip 47 engages socket 49, the first electrical contact is brought into proximity with the second electrical contact. The mutual proximity of the contacts is measured electrically using methods known in the art, so as to verify that the distal tip has engaged the socket.

Although the above preferred embodiments are described with reference to rings having flat or round cross-sectional profiles, it will be appreciated that other preferred embodiments of the present invention may comprise structures having other geometrical shapes and/or other cross-sectional profiles for placement of electrodes. The cross-sectional profile of the structure may be non-uniform. Furthermore, although the electrodes are shown in the figures as being attached externally to rings having smooth outer surfaces, in other preferred embodiments of the present invention, the rings may include recesses into which electrodes or other sensors are inserted.

In one such preferred embodiment of the present invention, the electrodes are placed on a structure comprising rigid and flexible, resilient sections. For insertion and removal of the catheter, the flexible sections bend, causing the structure on which the electrodes are placed to collapse into a narrow shape. The resilience of these sections, however, causes the structure to open out for making measurements once inside the heart.

Any desired geometrical structure may be used for electrode placement in accordance with the present invention, as long as the catheter and one or more devices for generating coordinate information are configured to allow determination of locations of all the electrodes. For example, in a preferred embodiment of the present invention comprising multiple devices for generating three-dimensional location information, one such device is placed adjacent to each of the electrodes, so that it is not necessary to explicitly determine the angular orientation of the structure holding the electrodes.

In some preferred embodiments of the present invention, the structure in which the electrodes are placed at the distal end of the catheter is polygonal, most preferably triangular. When the vertices of the polygonal structure are brought into contact with the endocardium, they will typically lodge in small crevices in the heart tissue, thus preventing the structure from moving during measurement, despite the natural motion of the heart. Preferably the electrodes are attached at or near the vertices.

Figure 10C:
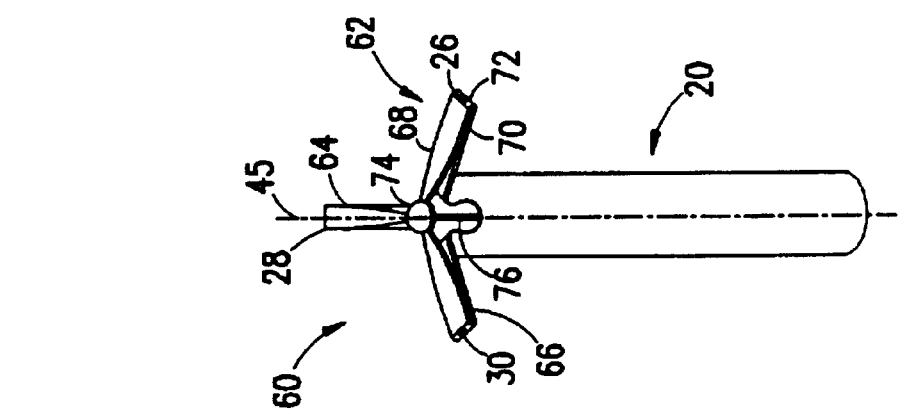
FIG. 10C is a perspective view of the catheter of FIG. 10A, shown in an open configuration suitable for performing electrophysiological measurements inside the body.
Figure 10B:
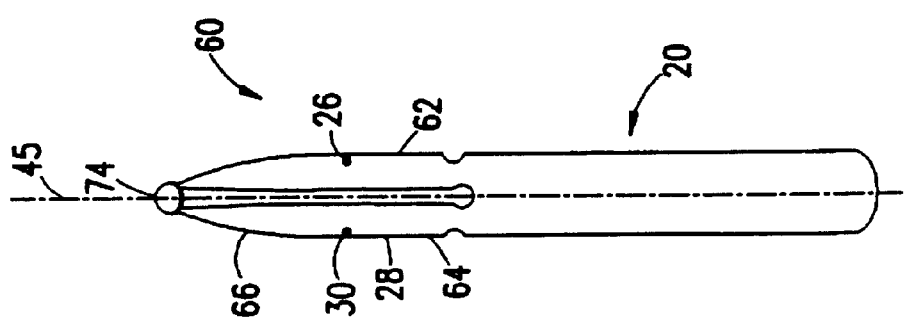
FIG. 10B is a perspective view of the catheter of FIG. 10A, shown in a closed configuration suitable for insertion into and removal from a human body.
Figure 10A:
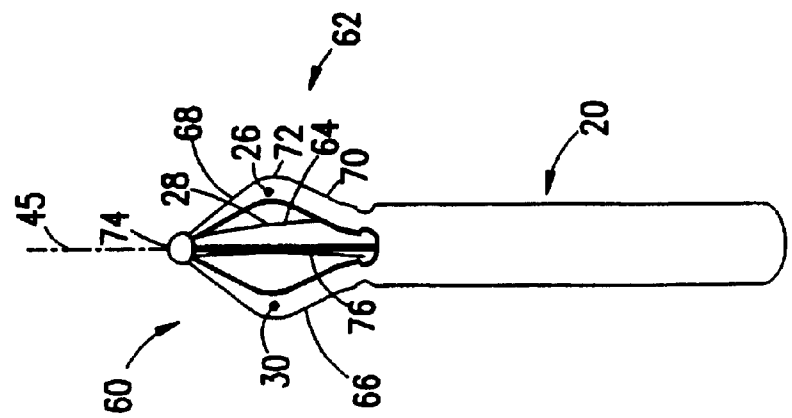
FIG. 10A is a perspective view of a catheter in accordance with still another preferred embodiment of the present invention, shown in transition from a closed configuration to an open configuration.

In another preferred embodiment of the present invention, shown in FIGS. 10A, 10B and 10C, structure 60 at the distal end of the catheter comprises multiple arms 62, 64 and 66. Electrodes 26, 28 and 30 are attached to the respective arms. As shown most clearly in FIG. 10A, arm 62 comprises two substantially rigid sections 68 and 70, which are joined by resilient joint 72. This joint is formed in such a manner that it causes sections 68 and 70 to maintain a mutual alignment that is substantially collinear, as shown in FIG. 10B, when no external forces are exerted thereon. (Although for the sake of simplicity, sections 68 and 70 and joint 72 are marked in FIG. 10A only with respect to arm 62, it will be understood that arms 64 and 66 are similarly constructed.) The arms are joined at their proximal ends to the distal end of catheter 20. The distal ends of the arms are joined together at flexible joint 74. Draw-wire 76 is also connected at its distal end to joint 74, and passes through a lumen of catheter 20 to its proximal end (not shown).

As shown in FIG. 10B, during insertion of catheter 20 into the heart or removal therefrom, draw-wire 76 is released, and the resilience of joints 72 causes sections 68 and 70 to maintain a substantially collinear mutual alignment, parallel to the long central axis 45 of the catheter. Once the catheter has been inserted into the heart, draw-wire 76 is pulled back toward the proximal end of catheter 20, exerting a proximally-directed force on flexible joint 74, and thereby causing resilient joints 72 to flex, as shown in FIG. 10A.

As shown in FIG. 10C, when draw-wire 76 is pulled completely into the catheter, joint 72 flexes by approximately 180° relative to its initial position (i.e., the position shown in FIG. 10B). Sections 68 and 70 assume a mutually adjacent positions, in substantially parallel mutual alignment, extending radially outward from and approximately perpendicular to catheter axis 45. In this configuration, electrodes 26, 28 and 30 may be brought into contact with the endocardium for measurement of electrical potentials. One or more devices for generating coordinate information (not shown in FIGS. 10A, 10B and 10C) may be fixed to structure 60 or adjacent to the distal end of catheter 20.

Figure 11A:
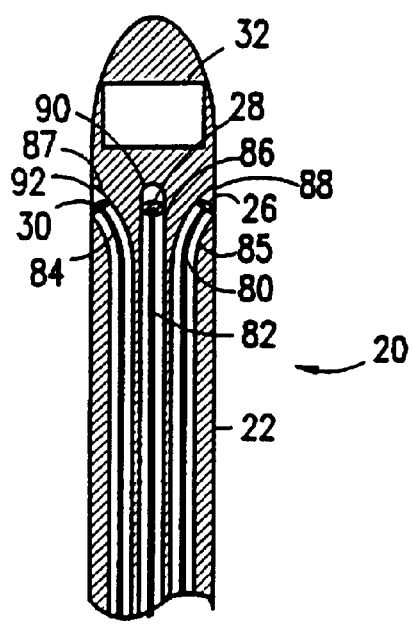
FIG. 11A is a schematic, cross-sectional view of a catheter in accordance with yet another preferred embodiment of the present invention, shown in a closed configuration suitable for insertion into and removal from a human body.
Figure 11B:
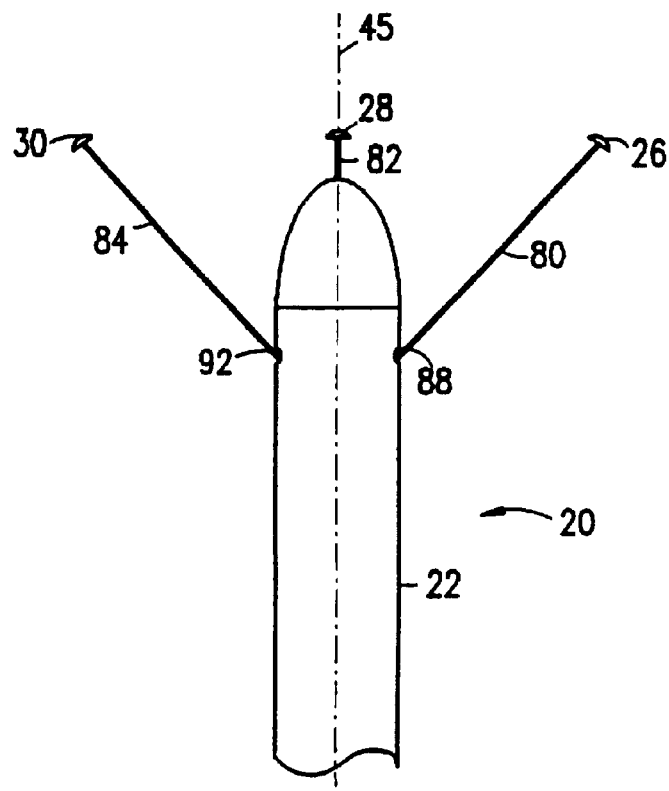
FIG. 11B is a perspective view of the catheter of FIG. 11A, shown in an open configuration suitable for performing electrophysiological measurements inside the body.

In another preferred embodiment of the present invention, shown in FIGS. 11A and 11B, electrodes 26, 28 and 30 are fixed adjacent to and aligned with the distal ends of substantially rigid arms 80, 82 and 84 respectively. As shown in FIG. 11A, during insertion of catheter 20 into the heart or removal therefrom the arms are contained inside respective lumens 85, 86 and 87 of the catheter, wherein the distal ends of the arms are adjacent to small radial openings 88, 90 and 92, respectively, in sheath 22 of the catheter. A device 32 for generating coordinate information is adjacent to the distal end of the catheter.

Once catheter 20 has been inserted into the heart, arms 80, 82 and 84 are pushed out through their respective radial openings, as shown in FIG. 11B. The resilience of the arms causes electrodes 26, 28 and 30 to assume predetermined positions, distal to the catheter's distal end and mutually-spaced about its long central axis 45.

Despite the flexibility of catheters, it is sometimes difficult to push the catheter smoothly through convolutions of certain vessels. In particular, the distal end of the catheter may chafe or scrape an inner surface of the vessel, not only making the insertion of the catheter difficult, but possibly causing damage to the vessel. Another possibility of damage occurs after the distal end of the catheter has entered an organ such as a chamber of a heart. Since the distal end is usually thin, care must be exercised to prevent accidentally puncturing, scraping or otherwise damaging inner walls of the organ.

Another problem relates to the possibility of formation of blood clots in cracks or sharp corners which are formed at the tip of the catheter.

One solution to these problems is to provide the catheter with a soft, smooth tip. In a preferred embodiments of the invention, the structure to which electrodes are fixed at the distal end of the catheter is coupled to an inflatable element, such as a balloon. After the catheter has been inserted into the heart, the inflatable element is inflated and causes the structure to assume a predetermined, known shape and orientation relative to the distal end of the catheter.

Figure 12B:
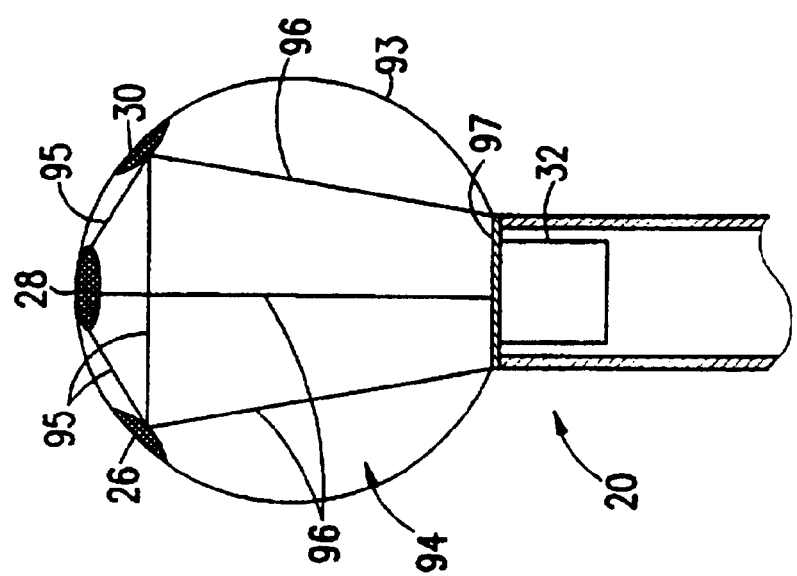
FIG. 12B is a schematic illustration of the catheter of FIG. 12A, shown in an expanded configuration suitable for performing electrophysiological measurements inside the body.
Figure 12A:
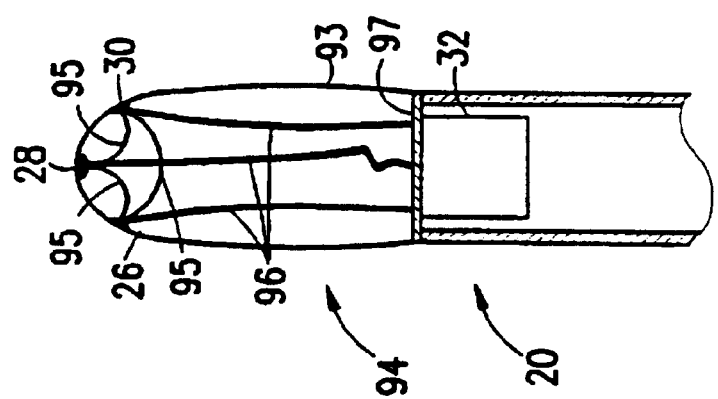
FIG. 12A is a schematic view of a catheter in accordance with still another preferred embodiment of the present invention, shown in a collapsed configuration suitable for insertion into and removal from a human body.

Thus, in a preferred embodiment of the present invention shown in FIGS. 12A and 12B, a catheter 20 comprises a balloon 93 at the catheter's distal end, wherein electrodes 26, 28 and 30 are attached to the surface of the balloon. The electrodes may be mechanically fastened to the balloon, or they may be chemically deposited on the balloon's surface using methods of electroplating or coating known in the art. Balloon 93 contains and protects a wire basket structure 94, which typically includes lateral wires 95 and axial wires 96 connected to electrodes 26, 28 and 30. Wires 95 and 96 are flexible, so that they may bend freely, but they are non-extensible, i.e., their length remains substantially constant when a tensile, stretching force is applied to them. Axial wires 96 are connected at their proximal ends to an anchor 97, which is in turn connected to a device 32 for generating coordinate information.

As shown in FIG. 12A, during insertion of catheter 20 into the heart, balloon 93 is deflated, thereby causing wires 95 and 96 to bend, so that basket structure 94 collapses into a narrow elongated shape.

Then, once the catheter is inside a chamber of the heart, as shown in FIG. 12B, balloon 93 is inflated by methods known in the art, such as by introducing a fluid into the interior thereof through a lumen of the catheter (not shown in the figure). Inflation of balloon 93 causes basket structure 94 to expand and become substantially rigid. When the balloon is fully inflated, wires 95 and 96 are pulled taut, so that electrodes 26, 28 and 30 assume known positions, relative to one another and relative to anchor 97, as determined by the lengths of wires 95 and 96. Because the wires are non-extensible, additional inflation of balloon 93 beyond the size necessary to straighten the wires will not affect the relative positions of the electrodes. For removal of the catheter from the body, balloon 93 is again deflated.

Figure 13B:
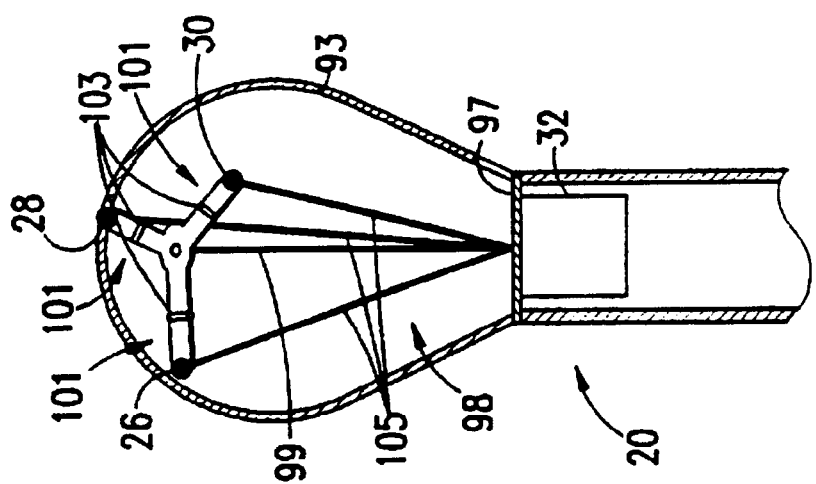
FIG. 13B is a schematic illustration of the catheter of FIG. 13A, shown in an expanded configuration suitable for performing electrophysiological measurements inside the body.
Figure 13A:
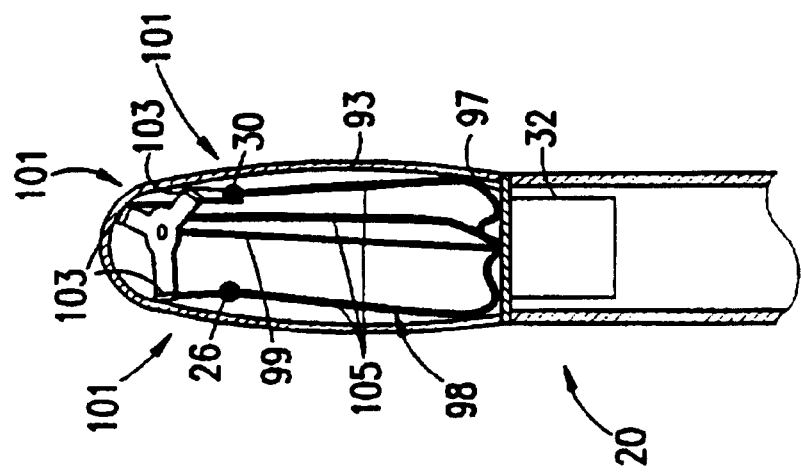
FIG. 13A is a schematic view of a catheter in accordance with another preferred embodiment of the present invention, shown in a collapsed configuration suitable for insertion into and removal from a human body.

In another preferred embodiment of the present invention, shown in FIGS. 13A and 13B, catheter 20 comprises at its distal end a balloon 93 and a collapsible structure 98. Structure 98 includes a substantially rigid axial member 99, which is contained inside balloon 93, and a plurality of radial members 101 coupled to the balloon on its outer surface. Radial members 101 comprise joints 103, so that when the balloon is deflated, as shown in FIG. 13A, the radial members fold down, and structure 98 assumes an elongated, narrow shape for ease of insertion into the body. Electrodes 26, 28 and 30 are fixed to the distal ends of radial members 101. Axial member 99 is attached at its proximal end to anchor 97, which is in turn connected to a device 32 for generating coordinate information. Structure 98 further comprises flexible, non-extensible wires 105, each of which is respectively attached at its proximal end to a point on axial member 99 or anchor 97, and at its distal end to a point adjacent to the distal end of a respective radial member 101.

As shown in FIG. 13B, after catheter 20 has been inserted into the heart, balloon 93 is inflated, thereby causing joints 103 to straighten, so that radial members extend radially outward from a central axis defined by axial member 99. When the balloon is fully inflated, wires 105 are pulled taut, thereby constraining joints 103 from bending any further than desired. Structure 98 thus becomes substantially rigid, so that electrodes 26, 28 and 30 assume known positions, relative to one another and relative to anchor 97, as determined by the structure. Because the wires are non-extensible, additional inflation of balloon 93 beyond the size necessary to straighten the wires will not affect the relative positions of the electrodes.

It should be appreciated that the electrodes deposited on the balloon may be of any desirable configuration, including, three unipolar electrodes, three bipolar electrodes, a line of electrodes. In addition, the balloon/structure may be adapted for a particular body structure, such as near the mitral valve, by suitable design of the inflated form of the balloon/structure.

Figure 14A:
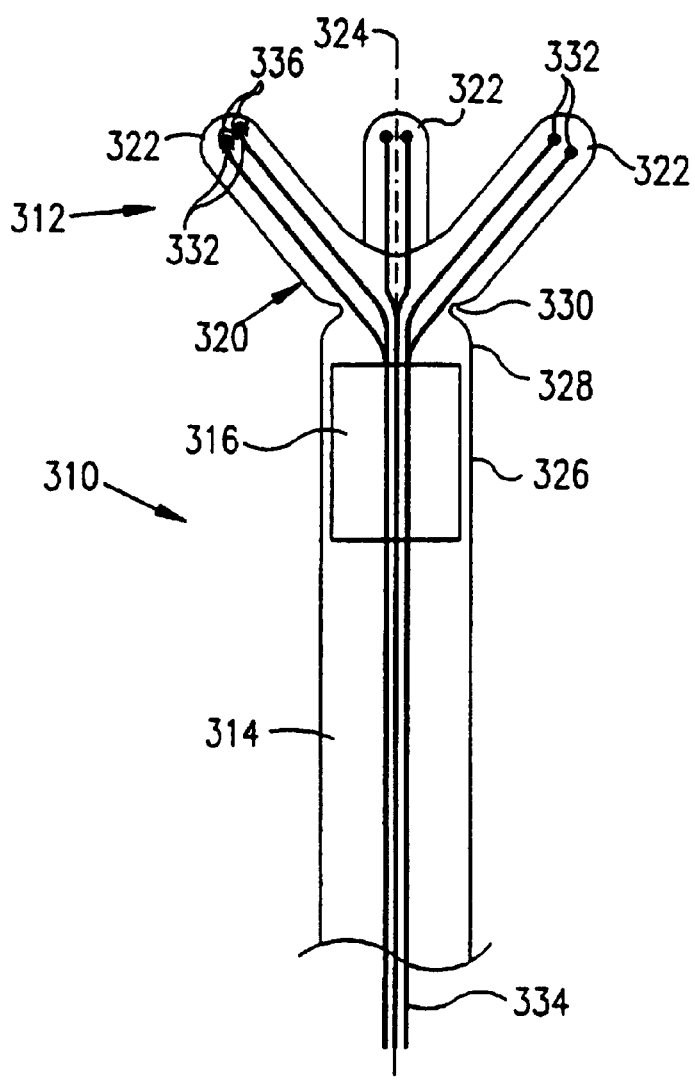
FIG. 14A is a simplified pictorial illustration of a catheter and a covering attached thereto, constructed and operative in accordance with a preferred embodiment of the present invention.

Reference is now made to FIG. 14A which illustrates a catheter 310 and a covering 312 attached thereto, constructed and operative in accordance with a preferred embodiment of the present invention.

Catheter 310 may any known type of catheter suitable for insertion into a body vessel, and preferably includes a tubular body portion 314 having a distal end 316.

Covering 312 preferably includes a resilient cap member 320 extending distally from distal end 316. Resilient cap member 320 preferably includes a tuft of distally extending, resilient lobes 322 with soft, smooth outer surfaces. Resilient cap member 320 is preferably constructed of an elastomeric material, such as rubber or latex. Lobes 322 are preferably substantially symmetrically arranged about a longitudinal axis 324 of catheter 310. FIG. 14A illustrates three lobes 322 substantially mutually spaced 120° apart about axis 324. It is appreciated that covering 312 may alternatively comprise any other number of lobes 322, including only a single off-axis lobe.

Preferably a sleeve 326 extends from a proximal end 328 of resilient cap member 320 and snugly fits over distal end 316 of the catheter. At least one radial dimple 330 is preferably formed at a juncture between sleeve 326 and the resilient cap member 320. In accordance with one aspect of the present invention, the radial dimple makes it easier for the lobes to bend backwards, by providing a volume to accommodate a portion of the lobe and enable a sharper bend angle with less stress on the cap. In accordance with a second aspect of the present invention, the dimple strengthens the connection between covering 312 and catheter 310.

Preferably at least one sensor 332 is fixed to resilient cap member 320. As seen in FIG. 14A, most preferably one or more sensors 332 are embedded inside each lobe 322. Sensors 332 may be any type of sensor useful in sensing a physiological activity. Sensor 332 may include a monopolar electrode or a bipolar electrode, useful for determining local electrical activity, such as local activation time. Alternatively or additionally, sensor 332 may include a strain gauge useful for determining muscle contraction. Sensors 332 may be in wired communication with sensor processing equipment (not shown) by means of wires 334 which are preferably embedded in lobes 322 along with sensors 332. Alternatively, sensors 332 may be capable of wireless transmission to sensor processing equipment (not shown).

In a preferred embodiment of the invention, a position sensor (not shown) is embedded in lobe 322, preferably near sensor 332, so as to more exactly determine the relative position of sensor 332.

One aspect of electrophysiological mapping is assuring that sensors 332 do not slip along the myocardium during the cardiac cycle. As shown in FIG. 14A, there may be provided at least one bump 336 which protrudes from lobe 322 of resilient cap member 20. All or a portion of lobes 322 may be provided with one or more bumps 336. Bump 336 is preferably integrally formed with lobe 322. In accordance with a preferred embodiment of the present invention, the bump 336 may include therein one or more of the sensors 332. It is appreciated that lobe 322 may have one sensor 332 inside bump 336 and another sensor 332 outside of bump 336. Bumps 336 may also serve to enhance the tissue contact and sensing capability of sensors 332. In particular it is understood that for best results in most sensing regimes a path from the sensor should be provided to the contact point on the surface of the myocardium. The nature of this path which may be a conducting path to the end of a bump, depends on the nature of the measurement being performed.

Figure 14B:
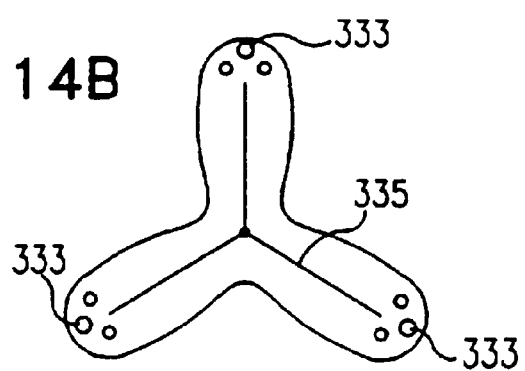
FIG. 14B is a front end view of the catheter of FIG. 14A

FIG. 14B shows a front view of catheter 310. The lack of any sharp angles in this embodiment should be appreciated. In a preferred embodiment of the invention, at least one opening 333 to a lumen is formed in each lobe 322. Such a lumen may be used to provide an extendible barb for attaching the lobe to the myocardium. Alternatively, such a lumen may be connected to a vacuum pump to provide anchoring via suction. Further alternatively, such a lumen may be used to provide irrigation to the region of sensor 332.

Preferably, anchoring means such as barbs and suction are applied only after sensor 332 is in good contact with the myocardium. The quality of contact is preferably determined using electrical activity signals and/or impedance signals from sensors 332.

In another preferred embodiment of the invention cap 320 includes a sensor 335 which generates indications of the relative positions of lobes 322. Sensor 335 may be a strain gauge which generates AC signals when lobes 322 move in relation to each other and/or in relation to catheter 310. Alternatively, sensor 335 may be a fiber-optic bend sensor. In one preferred embodiment of the invention, each of lobes 322 has an embedded sensor 335. Alternatively, all of lobes 322 are connected to a single sensor. In one preferred embodiment of the invention, local contraction time is determined based on the signal generated by sensor 335. It should be appreciated that binary information (constant strain/change in strain) is enough to determine the onset of such movement. However, preferably, the resolution of the signal from sensor 335 is sufficient to determine the relative positions of lobe 322 and cap 320.

In a preferred embodiment of the invention, local electromechanical mapping is performed even without a position sensor. One type of such mapping is viability mapping in which the relative timing of the electrical activation and the muscle contraction are compared. Further, such a strain gauge can be used in any of the multi electrode embodiments described herein.

Figure 15:
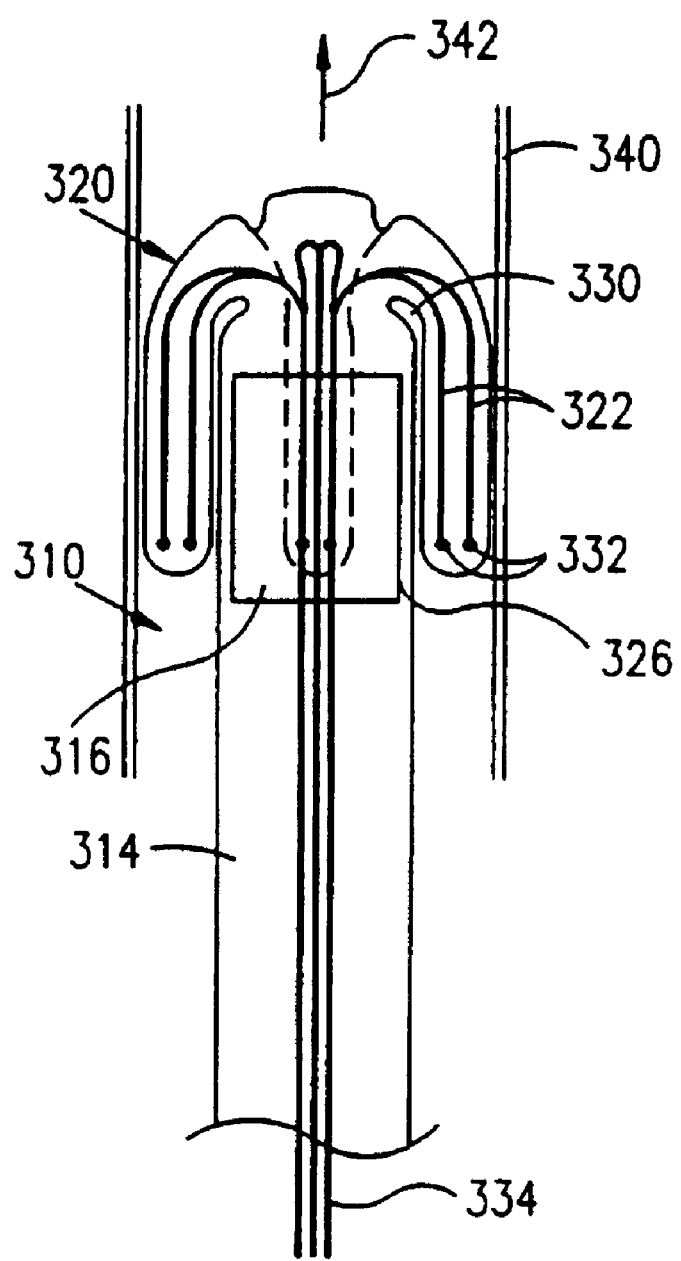
FIG. 15 is a simplified pictorial illustration depicting insertion of the catheter of FIG. 14A into a body vessel.

Reference is now made to FIG. 15 which illustrates inserting catheter 310 into a body vessel 340 in a distal direction, indicated by an arrow 342. Resilient cap member 320 and/or its lobes 322 are resiliently inverted over distal end 316 of catheter 310 during the distally directed motion of catheter 310 in vessel 340. Lobes 322 may be resiliently inverted prior to insertion of catheter 310 into vessel 340. Alternatively, lobes 322 are inverted when the lobes hit an obstruction in vessel 340. If the obstruction is small, catheter 310 will glide by it. However, if the obstruction is large, lobes 322 and/or cap 320 will be bent back by the pressure, such that the resulting streamlined tip will easily glide past the obstruction. The resilient inversion of resilient cap member 320 greatly facilitates insertion of catheter 310 into vessel 340, and provides a high degree of insertion safety, thereby substantially eliminating the possibility of catheter 310 scraping an inner surface of vessel 340. Because of radial dimple 330, there is substantially no build-up or bunching of material in the inverted state of lobes 322.

Upon proximally directed motion of catheter 310 in vessel 340, resilient cap member 320 once again becomes non-inverted and generally reverts to the shape illustrated in FIG. 14A. Alternatively, in some embodiment of the invention, cap 320 reverts to its previous shape (FIG. 14A) when it is unconstrained by vessel 340, for example, when entering the heart.

It should be noted that when catheter 310 is extracted from the body, lobes 322 form a streamlined shape which does not interfere with the extraction.

Figure 16:
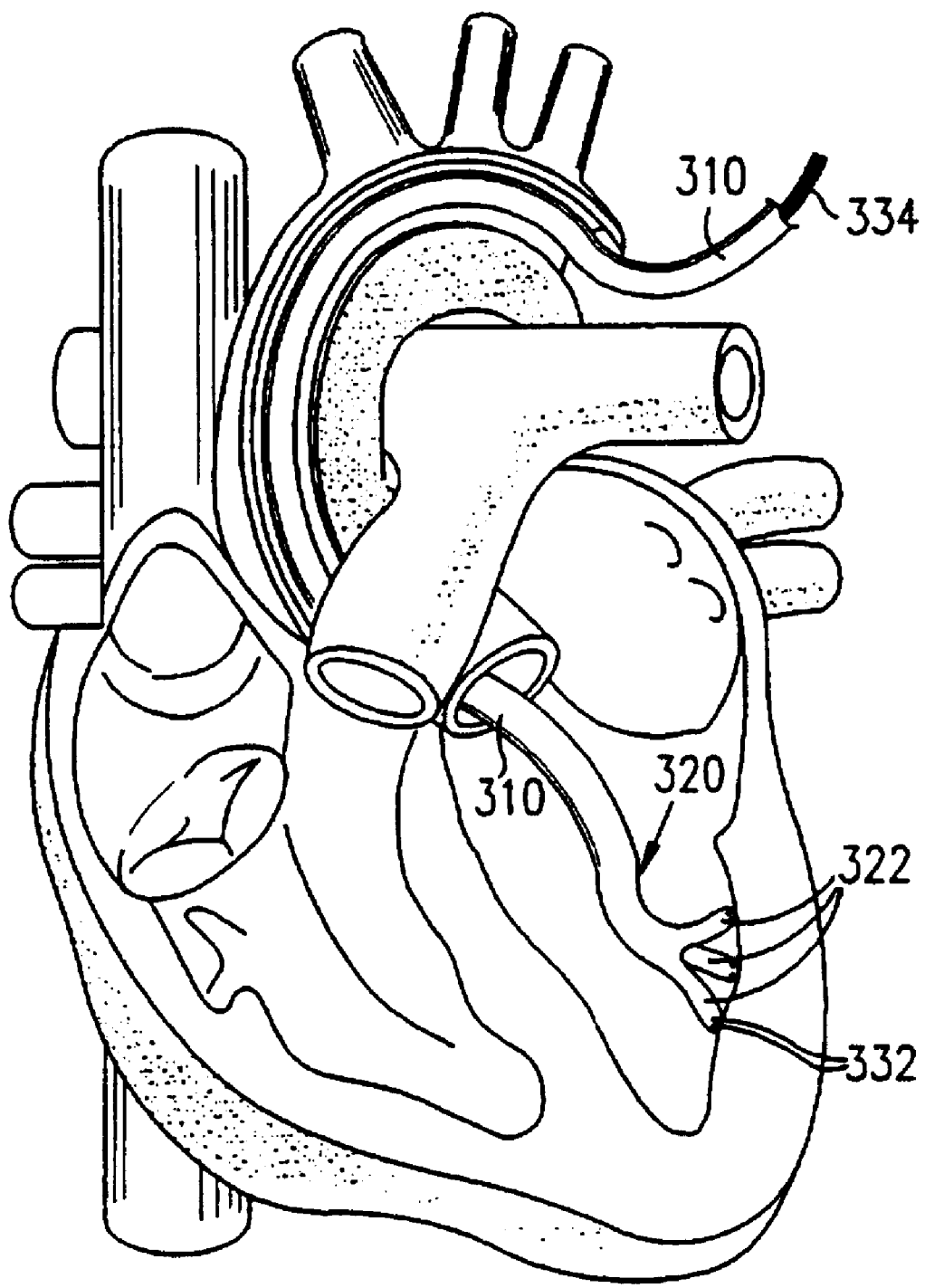
FIG. 16 is a simplified pictorial illustration of using the catheter of FIG. 14A to sense a physiological activity of tissue inside a body organ, in accordance with a preferred embodiment of the present invention.

Reference is now made to FIG. 16 which illustrates using catheter 310 to sense a physiological activity of tissue inside a body organ, in accordance with a preferred embodiment of the present invention. In FIG. 16, the body organ shown is a heart, but it is appreciated that the invention may be carried out for any other body organ as well. If the mapped organ is the brain, more flexible lobes are preferably used, as brain tissue is much weaker than vascular tissue and more liable to tear.

Catheter 310 is inserted into a body organ, such as a left ventricle of a heart, typically via the aortic valve. Catheter 310 is inserted so that sensors 332 contact a tissue, such as the endocardium. Depending on the type of sensor, it may be sufficient to bring sensor 332 in close proximity to the tissue without having to actually touch the tissue. Resilient cap member 320 substantially prevents accidentally puncturing, scraping or otherwise damaging inner walls of the left ventricle, by virtue of its large cross-section. Sensors 332 then sense a physiological activity of the tissue. Sensors 332 may sense the physiological activity substantially simultaneously, or alternatively, one at a time. Sensors 332 may sense, for example, a movement of the tissue, contraction time of the myocardium, or an activation signal of the myocardium. In this way, the contraction time of the heart muscle relative to the activation signal of the heart muscle, may be determined. As a further example, sensors 332 may sense velocity of fluid flow in or near the tissue. In a preferred embodiment of the invention catheter 310 comprises at least four non-coplanar pressure sensors, so that a true three-dimensional pressure gradient may be calculated. Such a pressure may be easily converted into a velocity vector, as known in the art.

In some preferred embodiments of the present invention, the device that generates coordinate information 32 generates six-dimensional position and orientation information. As noted earlier in reference to FIG. 2, device 32 may, for example, comprise a plurality of coils, and as described in PCT patent application number PCT/US95/01103, filed Jan. 24, 1995, which is assigned to the assignee of the present application and whose disclosure is incorporated herein by reference. Preferred embodiments of this device use a plurality of non-concentric coils, (not shown in the figures), adjacent to a locatable site in catheter 20, for example near its distal end, or on the structure on which electrodes 26, 28, 30 are placed, such as ring 24 or 44. These coils generate signals in response to externally applied magnetic fields, which allow for the computation of six location and orientation coordinates, so that the location and orientation of the catheter in the heart are known without the need for simultaneous imaging, by fluoroscopy or ultrasound, for example. Device 32 generates coordinate information relative to an external reference frame defined by electromagnetic field generator coils 27, which are fixed to the external reference frame.

Other preferred embodiments of the present invention comprise one or more devices for generating three-dimensional location information, as described, for example, in U.S. Pat. No. 5,391,199, to Ben-Haim, and PCT patent application PCT/US94/08352, which are assigned to the assignee of the present application and whose disclosures are incorporated herein by reference. One or more devices for generating location information are placed in the catheter or in the structure containing the electrodes, in proximity to electrodes 26, 28, 30. The respective location information generated by these devices is used to determine the positions of the electrodes.

In one such preferred embodiment of the present invention, two or more devices for generating three-dimensional location information are placed in known, mutually-spaced locations in the catheter or in the structure containing the electrodes, thereby allowing the positions of the electrodes in the structure to be determined.

The device disclosed in the aforementioned '539 patent application for generating three-dimensional location information preferably comprises a single coil in catheter 20. In preferred embodiments of the present invention that include a device of this type, the coil is toroidal in shape and coaxial with the long, central axis of the catheter. These embodiments thus have the advantage that the catheter may have one or more lumens, which pass through the opening at the center of the toroidal coil, while maintaining a relatively small external catheter diameter.

In some preferred embodiments of the present invention, a device that generates three-dimensional location information is placed in the catheter adjacent to the electrodes and is used to determine the location of the catheter inside the heart, while one or more rotation measuring devices measure the angular orientation of the catheter. The rotation measuring devices may be of any suitable type known in the art, such as, for example, shaft encoder devices adjacent to the proximal end of the catheter.

Figure 17:
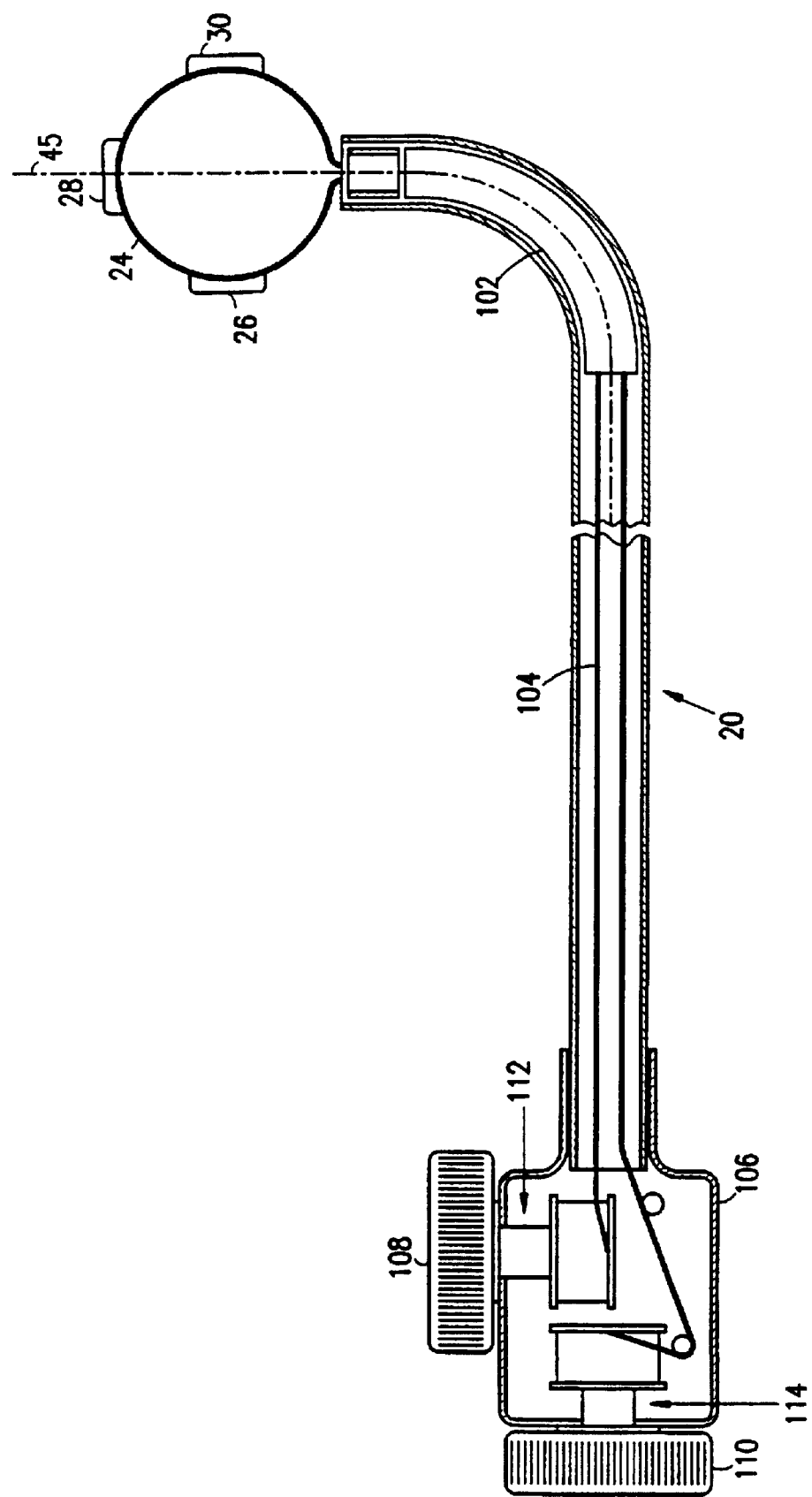
FIG. 17 is a schematic illustration of a catheter with a control handle, in accordance with a preferred embodiment of the present invention.

For example, in a preferred embodiment of the present invention shown in FIG. 17, a catheter 20 comprises at its distal end a substantially rigid ring 24 to which electrodes 26, 28 and 30 are fixed. The catheter further comprises a device that generates three-dimensional location information 100, which device preferably comprises a coil coaxial with the long central axis 45 of catheter 20. A tip deflection device 102, of a type known in the art, causes the distal end of the catheter to flex from side to side within a plane defined by ring 24, under the control of steering wire 104.

The operator of catheter 20 controls the catheter's movement using a handle 106 at the catheter's proximal end. Handle 106 includes a first control knob 108, which is coupled to steering wire 104 via a drum and thereby controls the flexing of tip deflection device 102, and a second control knob 110, which controls the rotation of the catheter about its long central axis 45. Shaft encoders 112 and 114 are coupled to knobs 108 and 110 respectively, and generate information regarding the tip deflection and rotation angles of the catheter. Since the positions of electrodes 26, 28 and 30 in ring 24 are known relative to the distal end of the catheter, the location information generated by device 100, taken together with the angles of rotation and deflection of the catheter as determined from the information generated by shaft encoders 112 and 114, is sufficient to track the location and orientation of ring 24 in the heart relative to a known starting position. If desired, the starting position may be verified by fluoroscopy or another imaging technique known in the art.

Figure 18B:
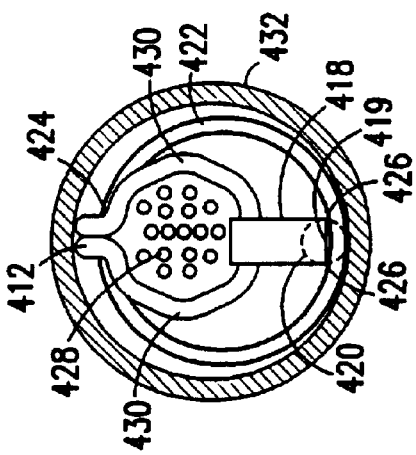
FIGS. 18A and 18B illustrate a steering mechanism in accordance with a preferred embodiment of the present invention.
Figure 18A:
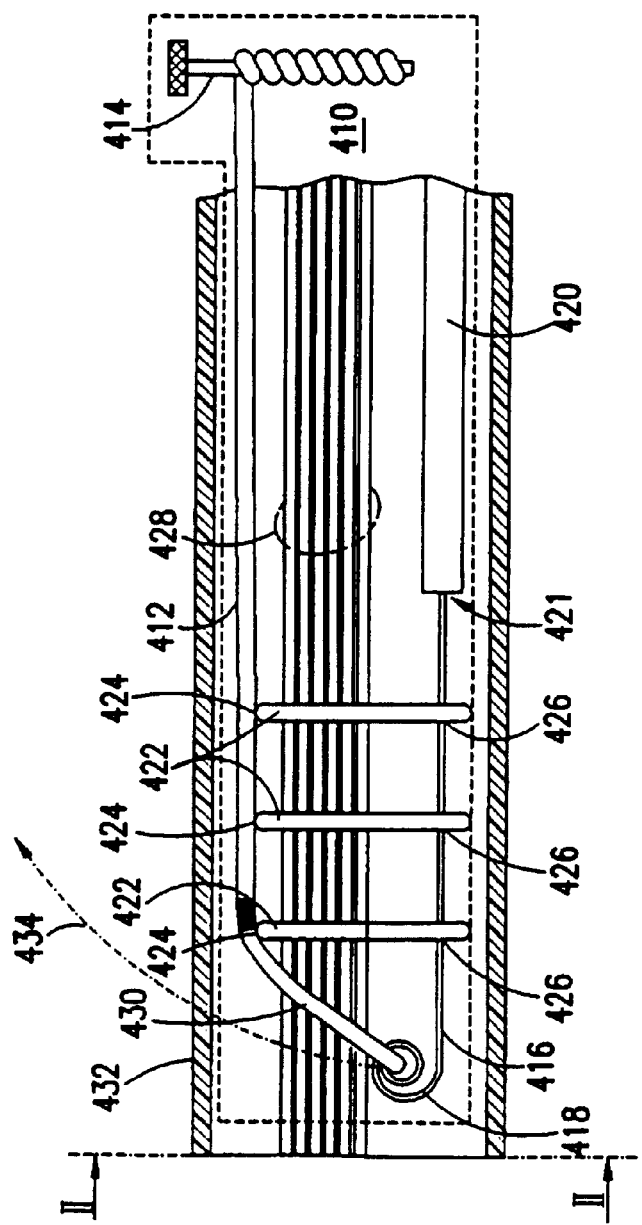

FIGS. 18A and 18B illustrate a catheter steering mechanism for a catheter 432 in accordance with a preferred embodiment of the invention. The mechanism, indicated by the dotted line, includes a stiffener 420 attached to a flat, flexible, elastic, member 416. The distal portion of member 416 is coiled into a spiral, through which a loop 430 is threaded. Loop 430 is formed at a distal end of a pull wire 412, which when pulled, cause flexible member 416 to bend, thereby bending the tip of catheter 432. Since member 416 is flat, it has a preferred bending plane perpendicular to its face, along arrow 434. The proximal end of pull wire 412 is preferably wound on a shaft 414, such that when shaft 414 is rotated, pull wire 412 is either tensed or relaxed, based on the turn direction. Pull wire 412 is preferably formed of Kevlar.

As is more clearly shown in FIG. 18B, loop 430 surrounds inner wires 428 of catheter 423. Wires 428 usually transmit sensor signals to and from the sensors and/or electrodes and or position sensors at the distal end of a catheter 432. A plurality of spaces 422 separate member 416 from pull wire 412, so that they do not get tangled together. It should be noted, that since wires 428 fill the bulk of catheter 432, spacers 422 may be flexible (but inelastic) and are also preferably formed of Kevlar.

In the preferred embodiment shown in FIG. 2, field generator coils 27 fixed to operating table 29 define an external reference frame, relative to which the position of position information generating device 32 is determined. In other preferred embodiments of the present invention, however, an external reference frame is defined and fixed relative to the heart muscle, as described, for example, by U.S. Pat. No. 5,391,199 and U.S. provisional patent application Ser. No. 60/009,769, filed Jan. 11, 1996, which are assigned to the assignee of the present application and whose disclosures are incorporated herein by reference. These disclosures teach apparatus and methods for mapping the interior of the heart using two catheters, each of which includes a device that generates coordinate information. One of the catheters is positioned in a predetermined, substantially fixed location in the heart, preferably at the apex of the heart, and serves as a reference catheter. By fixing the reference frame to the heart, errors in mapping of the heart that may arise due to the motion of the heart and chest are reduced.

Accordingly, in a preferred embodiment of the present invention, two catheters are inserted into heart 120. The first catheter 20 comprises ring 24 with electrodes 26, 28, 30 and coordinate information generating device 32 at its distal end, as described above. A second catheter, also comprises a coordinate information generating device adjacent to its distal end, and is positioned in a predetermined, substantially fixed location in a chamber of the heart, preferably at the apex of the heart. This second catheter thus defines a reference frame that is substantially fixed with respect to the heart, relative to which the position of the first catheter is determined.

This preferred embodiment has the advantage that errors in mapping the propagation of electrical impulses in the heart that may arise due to motion of the heart and chest are avoided, and furthermore that electrical propagation vectors, such as activation vector $\vec{V}$, may be mapped relative to an accurate map of the interior of the heart generated in accordance with U.S. Pat. No. 5,391,199 and U.S. provisional patent application 60/009,769, filed Jan. 11, 1996. The frame of reference defined by the second catheter also enables the operator to navigate the first catheter around the interior of the heart without the need for simultaneous fluoroscopic or other imaging.

In some preferred embodiments of the present invention, however, ultrasound or X-ray imaging may be used to determine the position of the first and/or second catheter in relation to the heart, so as to verify the reference points of the mapping of propagation of electrical impulses in the heart. In this case, the catheter to be imaged must include a suitable radio-opaque or ultrasound-reflecting marker.

In other preferred embodiments of the present invention, the field generator coils that provide the reference frame for coordinate information device 32 are fixed externally to the patient's body. Position detection is synchronized with an external electrocardiogram signal, so that the position is always detected at the same point in the heartbeat, and the influence of the heart's motion on the detected position of the catheter is neutralized.

In some such preferred embodiments, movements of the patient's thorax due to respiration are also detected, using methods known in the art, such as bio-impedance measurement. Position detection is synchronized with the respiration cycle, for example by accepting signals from coordinate information device 32 only at and immediately following maximum exhalation or only during the tail end of exhalation, so as to eliminate errors in position measurement that may generally arise as the result of such movements.

While the above preferred embodiments have been described with reference to measurement of electrophysiological signals in the heart, other preferred embodiments of the present invention may be used to measure and map electrical signals in the brain or in other physiological structures.

Furthermore, in other preferred embodiments of the present invention, other sensors, such as ionic sensors, may be used instead of the electrodes to perform localized measurements and map other aspects of physiological activity.

In a preferred embodiment of the present invention, for use in diagnosing and treating defects in the heart's electrical conduction, the distal end of the catheter is placed in proximity to the suspected site of a defect. On the basis of the vector direction and magnitude of the electrical propagation vector measured at this initial site, the catheter is then moved toward the suspected defect site. This procedure is repeated until the catheter reaches the actual site of the defect. Preferably, once the defect is located by the above procedure, it is ablated or otherwise treated by methods known in the art. It should be appreciated, that this procedure may be performed even without reference to a reference frame outside of the catheter.

In some preferred embodiments of the present invention, arrhythmias and pathological cardiac events are detected, using methods known in the art, simultaneously with determining the velocity vectors in accordance with the method described above. Each velocity vector is classified and stored, preferably by computer 51 or other electronic data storage device, according to a type of cardiac arrhythmia or event (or normal heart beat) that occurred at the time the electrogram signals used to determine the vector were received. Stored vectors that have been classified as belonging to a specific arrhythmia or event are then used to generate a map of the propagation of electrical activation in the heart that is characteristic of that arrhythmia or event. Such maps may be useful, for example, in detecting abnormal propagation of the activation front that is associated with a specific arrhythmia, including cases in which multiple activation fronts pass a location in the heart during a single R—R cardiac cycle interval.

It will be appreciated that the preferred embodiments described above are cited by way of example, and the full scope of the invention is limited only by the claims.

What is claimed is:

1. A method for determining a velocity relating to physiological activity at a location in a tissue, comprising:
   receiving signals indicative of physiological activity at a plurality of known positions adjacent to the location in the tissue;
   measuring a respective characteristic time at each of the plurality of positions using the signals received therefrom;
   computing velocity component vectors along two non-parallel axes, wherein the velocity component vectors are defined by the known positions and the measured activation times; and
   applying vector arithmetic operations to the velocity component vectors to determine the velocity at the location.

2. A method in accordance with claim 1, wherein each of the two non-parallel axes is defined by a respective pair of the known positions.

3. A method in accordance with claim 2, wherein each of the velocity component vectors has a magnitude determined by arithmetically dividing the distance separating the pair of known positions that define the respective axis of the velocity component vector, by the difference of the characteristic times between the known positions.

4. A method in accordance with claim 3, comprising finding one of the plurality of positions that has a characteristic time not substantially equal to the characteristic times of the other positions.

5. A method in accordance with claim 4, and comprising taking the position whose characteristic time is not substantially equal to the characteristic times of the other positions as a reference point for computing the velocity component vectors.

6. A method in accordance with claim 5, wherein both of the non-parallel axes are taken to pass through the reference point.

7. A method in accordance with claim 6, comprising identifying the location as a possible site of pathology if none of the plurality of positions is found to have a characteristic time that is not substantially equal to the characteristic times of the other positions.

8. A method in accordance with claim 7, comprising determining the velocity at the location relative to an external frame of reference.

9. A method in accordance with claim 8, wherein the signals are electrical signals, which are received by a plurality of electrodes at a plurality of known, respective positions.

10. A method in accordance with claim 9, and comprising fixing the electrodes at the distal end of a catheter, and inserting the catheter into a chamber of the heart of a subject, and wherein the velocity is a velocity of local electrical activation in the endocardium.

11. A method in accordance with claim 10, and comprising bringing the electrodes into contact with the endocardium, adjacent to the location at which the velocity is to be determined.

12. A method in accordance with claim 9, wherein the velocity is a measure of ionic current.

13. A method in accordance with claim 9, and comprising bringing the electrodes into proximity with a location in the brain, and wherein the velocity is a velocity of local electrical activation in the brain of a subject.

14. A method in accordance with claim 9, including mapping the velocity of local electrical activation in a plurality of locations in the endocardium, by determining the velocity at a plurality of known locations in the tissue, and recording the velocity thus determined as a function of the respective known locations.

* * * * *